(12) United States Patent
Portney

(10) Patent No.: US 6,342,058 B1
(45) Date of Patent: Jan. 29, 2002

(54) IRIS FIXATED INTRAOCULAR LENS AND INSTRUMENT FOR ATTACHING SAME TO AN IRIS

(76) Inventor: Valdemar Portney, 11940 N. Riviera, Tustin, CA (US) 92782

( * ) Notice: Subject to any disclaimer, the term of this patent is extended or adjusted under 35 U.S.C. 154(b) by 0 days.

(21) Appl. No.: 09/489,069

(22) Filed: Jan. 21, 2000

Related U.S. Application Data

(63) Continuation-in-part of application No. 09/312,566, filed on May 14, 1999, now Pat. No. 6,152,959.

(51) Int. Cl.$^7$ .................................................. A61F 9/00
(52) U.S. Cl. ...................................................... 606/107
(58) Field of Search ................................ 606/107, 166, 606/170, 205, 206; 623/905, 906

(56) References Cited

U.S. PATENT DOCUMENTS

| | | | | |
|---|---|---|---|---|
| 3,989,049 A | * | 11/1976 | Yoon | 128/326 |
| 4,215,440 A | | 8/1980 | Worst | |
| 4,435,855 A | | 3/1984 | Pannu | |
| 4,542,540 A | | 9/1985 | White | |
| 4,542,541 A | | 9/1985 | Pannu | |
| RE32,525 E | | 10/1987 | Pannu | |
| 4,706,666 A | * | 11/1987 | Sheets | 128/303 |
| 5,135,530 A | * | 8/1992 | Lehmer | 606/107 |
| 5,192,319 A | | 3/1993 | Worst | |
| 5,222,960 A | * | 6/1993 | Poley | 606/107 |
| 5,395,378 A | * | 3/1995 | McDonald | 606/107 |
| 5,618,307 A | * | 4/1997 | Donlon et al. | 606/205 |

OTHER PUBLICATIONS

ARTIS AN™ Phakic Intraocular Lenses "Focus on Perfection" Ophtec Laboratories (75 sheets).

* cited by examiner

Primary Examiner—Eduardo C. Robert
(74) Attorney, Agent, or Firm—Howard R. Lambent

(57) ABSTRACT

An iris fixated intraocular lens for implanting in the anterior chamber of an eye comprises an optic having an optical axis and anterior and posterior sides; and first and second fixation members, each of the fixation members having a proximal end region and a distal end region. The proximal end region of each fixation member is a single flexible strand fixed to an edge region of the optic to extend generally tangentially outwardly therefrom and the distal end region is formed into a loop having defined therein at least one narrow iris pincher gap for detachably attaching the intraocular lens to the anterior surface of the iris. The first and second fixation members are substantially identical to one another and are attached to the optic on opposite sides of the optical axis. The optic is preferably constructed from an elastically deformable plastic material, such as silicone or an acrylic, so that the resulting three-piece intraocular lens can be folded or otherwise deformed for implanting into an eye through a small, preferably sutureless, surgical incision. Variation IOLs are disclosed, such variations relating to iris pincer gaps. A combination enclavation needle and forceps instrument, capable of one-handed use, is also disclosed. The instrument may be primarily electrically or mechanically operated.

30 Claims, 17 Drawing Sheets

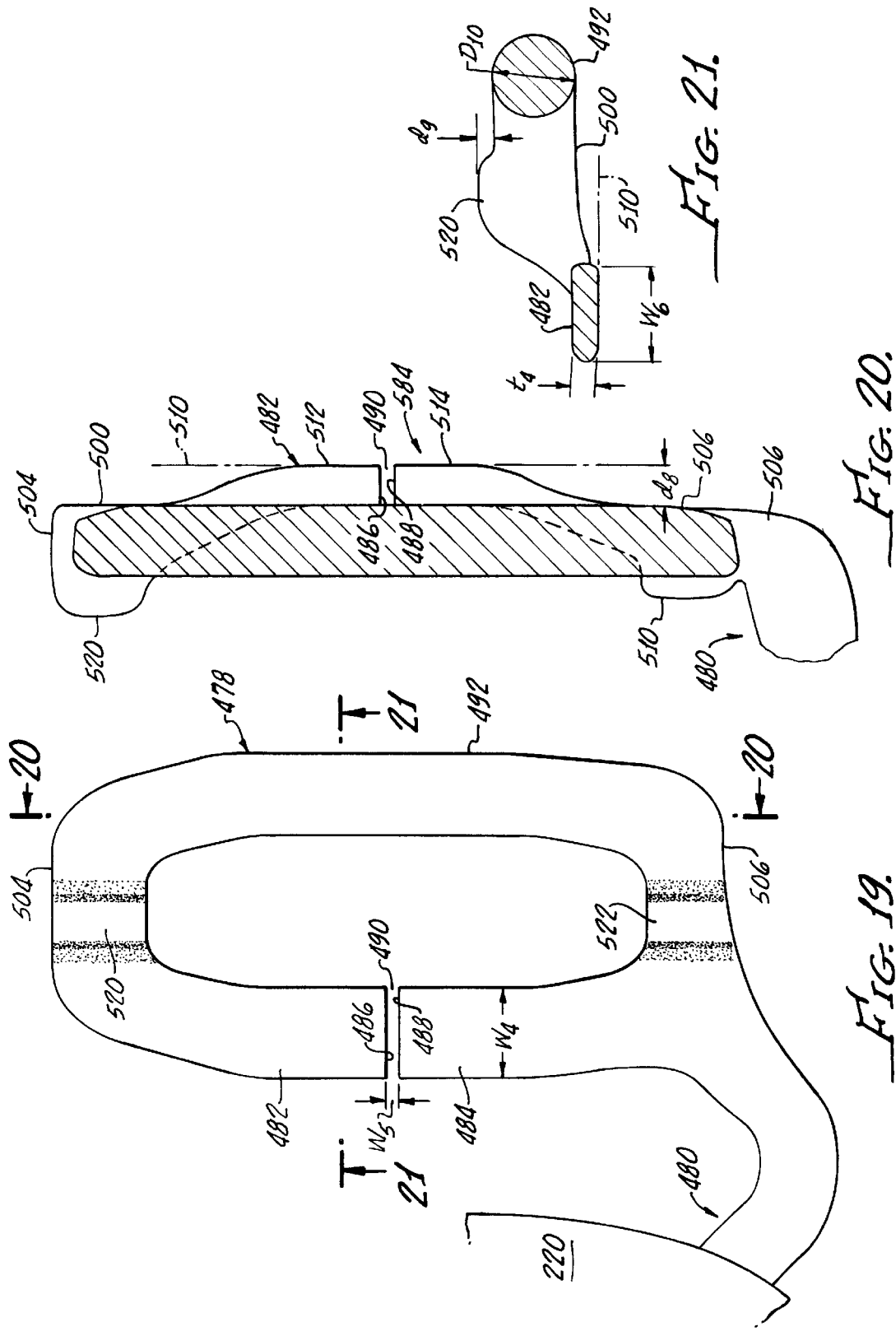

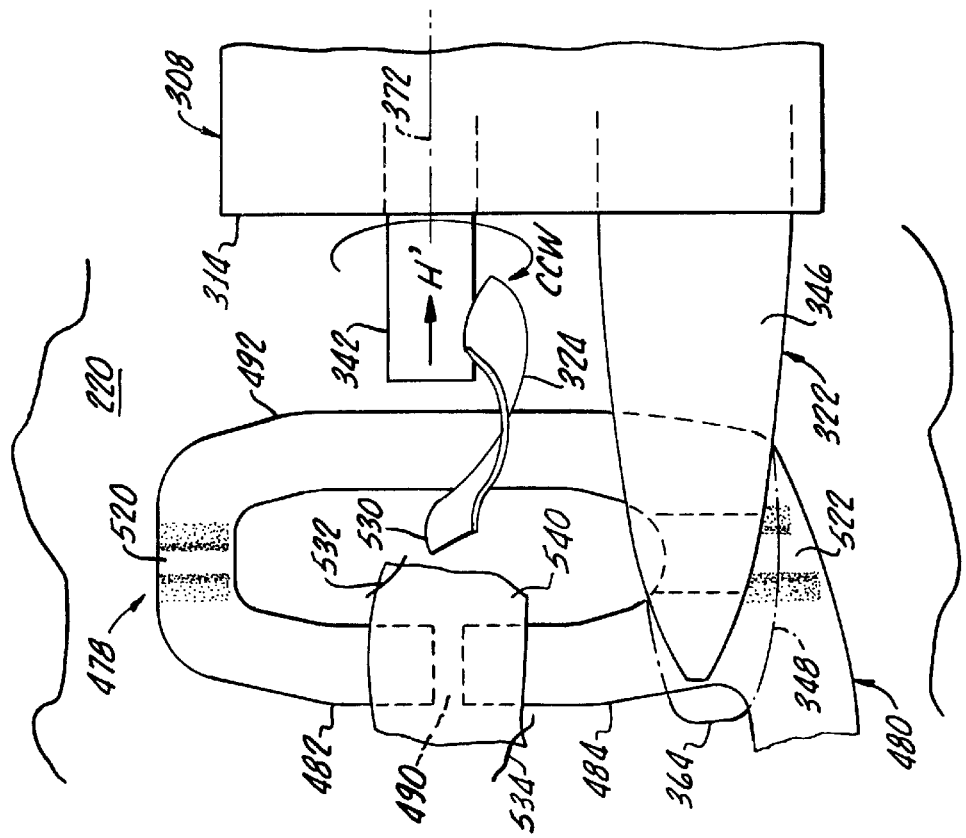

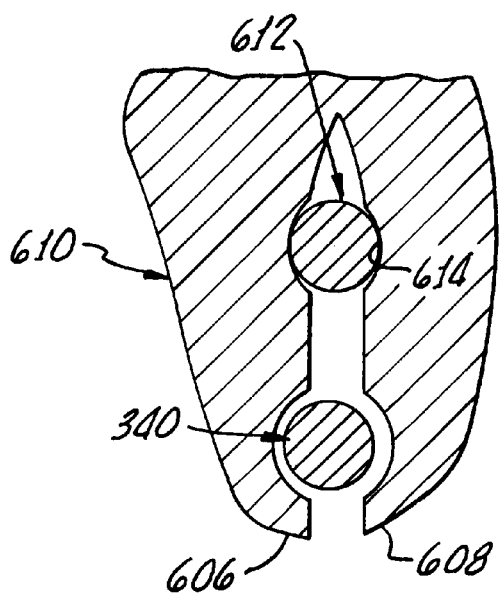
_FIG. 24._
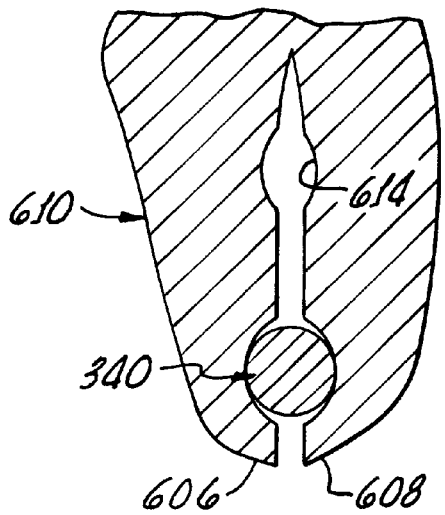
_FIG. 26._

IRIS FIXATED INTRAOCULAR LENS AND INSTRUMENT FOR ATTACHING SAME TO AN IRIS

This application is a continuation-in-part of application Ser. No. 09/312,566, filed May 14, 1999. Now U.S. Pat. No. 6,152,959.

BACKGROUND OF THE INVENTION

1. Field of the Invention

The present invention relates generally to the field of ophthalmics, more particularly to ophthalmic devices, still more particularly to ophthalmic devices known as intraocular lenses (IOLs), and even more particularly to iris fixated intraocular lenses and to surgical instruments useful for attaching such lenses to an ocular iris.

2. Background Discussion

At the onset it may be helpful to the understanding of the present invention to define the terms "phakic" and "aphakic" as related to human eyes. The term "phakic" is applied to an eye in which the natural ocular lens is still present. This is in contrast to an "aphakic" eye from which the natural ocular lens has—for any reason—been removed. A phakic eye is considered a dynamic or active eye because the living natural lens is subject to change over time, while an aphakic eye is considered a static eye because the natural lens has been removed.

Vision in an eye is enabled by light from a viewed image being refracted to the retina by the cornea and the natural lens (and/or any implanted intraocular lens) located posterior of the cornea.

One relatively common ocular problem is impaired or complete loss of vision due to the natural ocular lens becoming cloudy or opaque—a condition known as cataract. The formation of cataracts is typically associated with natural bodily aging, and most individuals over the age of about 60 years suffer from cataracts at least to some extent.

Cataracts cannot currently be cured, reversed, or even significantly arrested. Accordingly, the corrective action involves surgically removing the natural lens when the lens becomes so cloudy that vision is greatly impaired, the result being that a phakic eye becomes an aphakic eye.

After a defective natural lens has been surgically removed, the current vision-restoring practice (since about the 1940's) is to implant in the aphakic eye an artificial refractive lens called an intraocular lens (IOL) having an optic and optic fixation means. previously, thick, heavy, high diopter spectacles were prescribed for aphakic eyes. Such spectacles however were and still are generally disliked by most patients for their weight and appearance.

Implantable IOLs were initially constructed from rigid polymethyl methacrylate (PMMA) a hard, biocompatable plastic material. More recently, IOLs have been constructed from a soft, elastically deformable, silicone or acrylic material that enables insertion of the IOLs through small ocular incisions.

In addition to the implanting of IOLs in aphakic eyes to restore vision after removal of the natural lens, considerable interest has recently arisen in implanting IOLs in phakic eyes to correct myopia, hyperopia, presbyopia or astigmatism problems associated with non-cataract natural lenses. This implanting of corrective IOLs in phakic eyes is an often-attractive alternative to the wearing of corrective spectacles or contact lenses, which limit certain activities and even certain professions, or having performed such surgical procedures on the cornea as radial keratomy (RK) or photoradial keratectomy (PRK), which may not be desired by many individuals for various reasons. The implanting of refractive IOLs in phakic eyes to correct vision problems is considered to constitute one of the remaining frontiers of vision correction.

In an aphakic eye, a replacement IOL is now typically implanted in the posterior chamber of the eye from which the natural lens has been removed. In contrast, a corrective IOL for a phakic eye is most desirably implanted in the anterior chamber of the eye, forwardly of the intact natural lens remaining in the posterior chamber of the eye. (In some difficult cases, however, an IOL may be implanted in the anterior chamber after the natural lens has been removed from the posterior chamber.) The former type of IOL is called a posterior chamber IOL and the latter type is called an anterior chamber IOL. There are significant construction differences between these two types of IOLs.

With specific regard to anterior chamber IOLs (with which this application is concerned), there has been recently renewed interest in IOLs constructed for fixation to the iris for correcting vision in phakic eyes (although, some of the earliest IOLs for aphakic eyes were iris fixated anterior chamber IOLs). One reason for renewed interest in iris fixated IOLs for phakic eyes is that fixating (i.e., attaching) the optic supporting structure directly to the iris itself avoids contact by the IOL with the sensitive filtration angle of the eye, thereby reducing subsequent ocular problems.

Iris fixated IOLs are disclosed in recent U.S. Pat. Nos. 4,215,440 and 5,192,319 to Jan Worst. Both of such patents disclose IOLs employing one or more optic fixation members formed having a pair of pincer arms which, by surgical manipulation when attaching the IOLs to an iris, pinch up and hold a small, anterior surface region of the iris in the narrow gap between the pincer arms. This pinching action detachably attaches the IOL to the iris so that the IOL optic is (ideally) fixated in the region of the iris opening (i.e., the pupil of the eye).

However, the present inventor considers that improvements to the iris fixated IOL designs disclosed in the two above-cited Worst patents are desirable. It is, therefore, a principal objective of the present invention to provide such improvements, particularly in the areas of improving optic centration and enabling small incision implanting of iris fixated IOLs.

Moreover, so far as is known to the present inventor, the attaching to the anterior surface of the iris of iris fixated IOLs of the type disclosed by the above-referenced Worst patents has involved a very tedious and difficult two-handed procedure requiring great skill, dexterity, and training.

In this regard, a forceps is used by one of the IOL implanting surgeon's hand to hold the IOL with the IOL optic centered on the iris. The surgeon uses his other hand to manipulate a needle (called an enclavation needle) to capture and lift a small region of iris stromal tissue adjacent the gap between the pair of pincer arms of one of the IOL fixation members (haptics).

This lifting of iris tissue in the gap region lifts opposing end regions of the pincer arms, thereby causing widening of the gap between the pincer arms. Thus, when the tip of the enclavation needle is withdrawn from the iris tissue, the lifted region of tissue becomes pinched in the narrowing gap between the pincer arms as the arms flex back downwardly to their normal position. This procedure results in the attachment of the related IOL fixation loop to the iris.

As a next step, the forceps and enclavation needle are switched between the surgeon's hands to perform the same attachment procedure for the second IOL fixation loop to the iris and the resulting attachment of the IOL to the iris.

This two-handed (i.e., bi-manual) IOL-to-iris fixation procedure is not only extremely difficult and very dependant upon the surgeon's skill, but it does not leave a free hand of the surgeon to perform other, ancillary procedures associated with the surgical implant of the iris fixated IOL.

It is therefore a principal objective of the present invention to provide a combination forceps and enclavation instrument, which enable both the forceps and needle to be operated in a relatively simple manner with one hand. This new combination instrument greatly simplifies the attachment of the above-described types of iris fixated, poster chamber IOLs to an iris and reduces the level of surgical skill required for performing the IOL to-iris attachment procedure.

SUMMARY OF THE INVENTION

In accordance with the present invention, there is provided an iris fixated intraocular lens which comprises an optic having an optical axis and anterior and posterior sides and at least two fixation members, and which may have an overall diameter of between about 7.5 mm and about 10 mm. Each of the fixation members have a proximal end region and a distal end region, the proximal end region comprising a flexible strand, preferably, a single flexible strand, fixed to an edge region of the optic so as to extend generally tangentially outwardly therefrom. The distal end region is formed into a loop having defined therein at least one narrow iris pincher gap.

In a preferred embodiment of the invention, the at least one pincher gap is located on a line generally perpendicular to the optical axis, but may alternatively be formed at an angle to the perpendicular line.

It is preferred that the at least two fixation members include first and second fixation members that are substantially identical to one another and are attached to the optic on opposite sides of the optical axis. The first and second fixation members are constructed separately from the optic, the intraocular lens being thereby a three-piece intraocular lens.

It is further preferred that the optic is constructed from an elastically deformable material, which may be a silicone material or an acrylic material. Also, the at least two fixation members lie in an at least substantially common plane located posterior of the optic.

The distal end loop of each of the at least two fixation members may be elongated into a curved shape, and in some embodiments of the invention, each of the distal end loop includes means dividing the loops into first and second segments; in which case, a first pincer gap is defined in the first loop segment and a second pincer gap is defined in the second loop segment. Preferably, the loop dividing means lies generally perpendicular to the optical axis of the optic.

The at least one pincer gap preferably has a width of between about 0.05 mm and about 0.25 mm, and preferably has a length between about 0.2 mm and about 0.5 mm. The pincer gap in the distal end loop of each of the first and second fixation members may be located in a region of the loop closest to said optical axis, or in a region of the loop furthest from said optical axis. In either case, the pincer gaps are spaced a preferred distance between about 8.0 mm and about 9.0 mm away from the optical axis of the optic.

Because the fixation members are constructed as a flexible strand and the optic is constructed from an elastically deformable material, the resulting three-piece iris fixated IOL of the invention can be folded, rolled or otherwise deformed for insertion through a small, sutureless incision in the eye, as is highly desirable for such reasons as minimal patient trauma and the reduced possibility of surgical complications. Also importantly, the flexible strand fixation members enable accurate centration of the associated optic in the patient's eye upon fixation of the IOL to the iris.

There is additionally provided a combination forceps and enclavation needle instrument, preferably, a hand-held instrument, for use in attaching a fixation loop of an anterior chamber intraocular lens (IOL) to the anterior surface of a human ocular iris, the fixation loop having a narrow iris tissue pincer gap defined therein and having thickened end regions.

The combination instrument comprises a handle portion sized for being held in one hand of a user, the handle having an outer wall and a slender ocular insertion portion having an open distal end, the insertion portion being connected, preferably detachably connected, to the handle portion. The insertion portion is preferably eliptical or oval in transverse cross section with a major cross sectional dimension no greater than about 2.5 mm.

Included in the instrument is a forceps tip projecting from the insertion portion open distal end, the forceps tip having first and second IOL gripping jaws connected for gripping the IOL fixation loop. Preferably, the first forceps tip jaw projects further than said forceps tip second jaw from the insertion portion open distal end. Further included is an enclavation needle tip projecting from the insertion portion open distal end configured for engaging iris tissue and for lifting the engaged iris tissue into the fixation loop pincer gap.

Operating and control means are connected for selectively causing the forceps tip jaws to open and close, for selectively moving the needle tip between a lifted position and a lowered position, and for selectively causing partial rotation of the needle tip in clockwise and counterclockwise directions.

The operating and control means preferably include moving means for moving the forceps tip and needle tip in unison in a selected axial direction.

In a preferred embodiment, the needle tip has an axial helical shape with a sharp distal end and the operating and control means include means for simultaneously moving the needle tip in an axial direction and for rotating the needle tip.

In one version of the combination instrument, the operating and control means include an electric power source, a plurality of reversible electric motors and a plurality of electrical switches connected for providing electrical power to the motors from the power source. Preferably, each of the electrical switches comprises a momentary on-off-momentary on switch having a manually operated portion projecting outwardly from the instrument handle portion. In such case, the manually operated switch portions project outwardly from the handle portion in locations enabling the operation thereof by one hand of an operator holding the handle portion without the necessity of repositioning the hand.

Alternatively, the operating and control means may include a plurality of manually operated thumb wheels that also extend outwardly from the handle portion in locations enabling the operation thereof by one hand of an operator holding the handle portion.

The operating and control means include a first, elongate slender control pin connected to the needle tip and a second, elongate slender control pin pivotally connected to one of the forceps tip jaws, preferably, the second jaw. The operating and control means further include a sleeve slidably disposed around the first control in and a third, elongate slender control pin connected to the sleeve. Means are then provided for pivotally connecting the sleeve to the insertion portion so that axial movement of the third control pin causes the raising or lowering of the sleeve and needle tip.

Further comprising the operating and control means are a first connecting pin detachably connected to the first control pin, a second connecting pin detachably connected to the second control pin and a third connecting pin detachably connected to the third control pin. Also included are respective first, second and third pairs of gears operatively connected to corresponding ones of the first, second and third connecting pins, as well as respective first, second and third reversible electric motors connected to corresponding ones of the first, second and third pairs of gears.

Respective first, second and third thumb wheels mat be connected to corresponding ones of the first, second and third pairs of gears in place of the electric motors.

The combination enclavation needle and forceps instrument of the present invention—since the dualfunction instrument is configured for one-handed operation—is intended to significantly reduce the level of skill required to fixate an anterior chamber IOL to an anterior surface of an iris over that required when individual enclavation needles and forceps requiring two-handed operation are used, as heretofore has been the case. In addition, and importantly, the combination instrument of the present invention is intended to assure reproducibility of iris fixated IOL fixation procedures.

It may nevertheless sometimes be desirable to provide a generally corresponding single-function instrument having only a needle tip or only a forceps tip because of the easy control provided. In such cases, the associated operating and control means would be limited for operating and controlling to whichever tip is provided.

BRIEF DESCRIPTION OF THE DRAWINGS

The present invention can be more readily understood by a consideration of the following detailed description when taken in conjunction with the accompanying drawings, in which:

FIG. 11 is a series of cross sectional views taken along line 11—11 of FIG. 10.

FIG. 18 is a series of enlarged drawings showing several different shapes of enclavation needle tips.

FIG. 19 is a greatly enlarged plan view of a modified haptic fixation loop of the iris fixated IOL similar to that depicted in FIG. 2, the fixation loop being configured to facilitate operation of the combination forceps and enclavation needle instrument, the fixation loop having thickened end regions for rigidity;

FIG. 20 is a cross sectional view taken along line 20—20 of FIG. 19, showing end regions of the fixation loop raised relative to central regions of the loop;

FIG. 21 is a cross sectional view taken along line 21—21 of FIG. 19, showing a representative one of thickened end regions of the fixation loop;

FIG. 22 is a series of drawings depicting, by way of specific example, operation of the combination forceps and enclavation needle instrument of the present invention in connection with the haptic fixation loop depicted in FIGS. 19–21; with the helical needle tip depicted in FIG. 18A and with the insertion portion of the instrument positioned at a right angle relative to a long axis of the fixation loop: FIG. 22C being similar to FIG. 22B, but depicting further CCW rotation of the needle tip to lift the engaged iris tissue into the pincer arm gap that is also lifted and widened by the lifted iris tissue; and FIG. 22D depicting the needle tip partially rotated back in the CW direction and retracted in the direction of Arrow "E" to thereby withdraw the needle tip from the engaged iris tissue, leaving the previously uplifted region of iris tissue pinched (i.e., trapped) in the pincer arm gap;

FIG. 24 is a transverse cross sectional drawing looking along line 24—24 of FIG. 23 showing the associated clamping member for the forceps tip control pin in unclamped configuration;

FIG. 26 is a transverse cross sectional drawing looking along line 26—26 of FIG. 25 showing the associated clamping member clamping the forceps tip control pin.

In the various FIGS., the same elements and features are given the same reference numbers. In the various variation variations, corresponding elements and features are given the same reference numbers as first set forth, followed by an "a", "b", "c", and so on, as appropriate and/or as will be evident in the following DESCRIPTION.

DESCRIPTION OF THE PREFERRED EMBODIMENT

Figure 1:
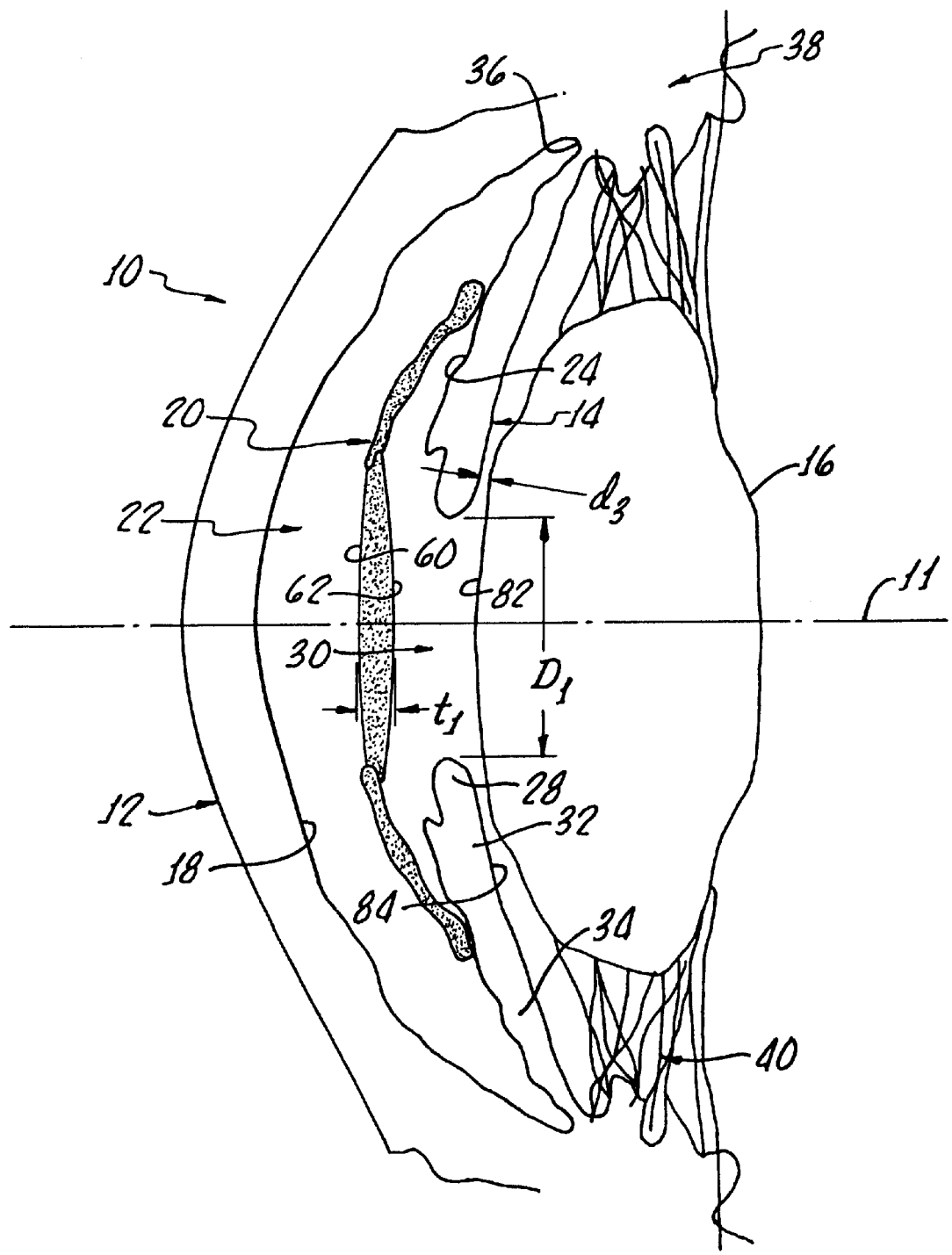
FIG. 1 is a vertical cross sectional drawing of forward regions of a representative human eye, showing the cornea, iris and natural lens and showing an iris fixated intraocular lens (IOL) of the present invention implanted in the anterior chamber of the eye and fixed to the anterior surface of the iris.

There is shown in FIG. 1, in vertical cross section, a forward region 10 of a representative human eye having an optical axis 11 (Axis of symmetry). Depicted in the FIG. are a cornea 12, an iris 14 and an intact, natural crystalline lens 16. A (posterior) corneal endothelium surface 18 is identified on cornea 12

An iris fixated intraocular lens (IOL) 20, according to a preferred embodiment of the present invention, is shown implanted in an anterior chamber 22 of eye region 10 (posterior to corneal endothelium surface 18) and fixated, in a manner described below, to an anterior surface 24 of iris 14.

Identified in FIG. 1, to facilitate the understanding of the present invention, is an annular pupiliary spincter region 28 of iris 14 that surrounds and controls a pupil or pupiliary opening 30 having a diameter, $D_1$, that typically no greater than about 8 mm for normal vision.

Further identified are an annular iris collarette region 32 and an annular pupiliary dilator muscle region 34 of iris 14. An annular chamber angle 36 is identified at a peripheral edge region of iris 14, as is an annular trabecular meshwork 38. An annular ciliary process 40 is indicated at the peripheral attachment of natural lens 16.

As is further depicted in FIG. 1, iris fixated IOL 20 is fixated to iris anterior surface 24 in the general region of iris collarette 32 (the thickest region of iris 14), radially outwardly from pupiliary sphincter 28.

Figure 2:
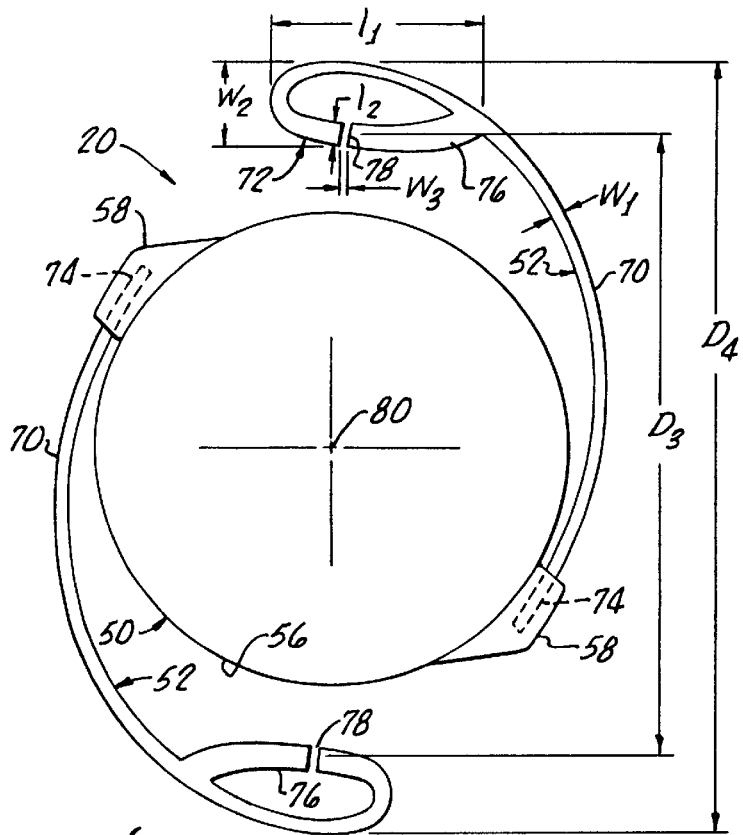
FIG. 2 is a front view of one embodiment of a three piece iris fixated IOL of the present invention, showing the optic and an opposing pair of optic support or fixation members (haptics), each terminating in an elongated fixation loop having a narrow pincer gap for enabling detachable attachment of the IOL to the anterior surface of a patient's iris, the pincer gaps being shown directly facing the optic.
Figure 3:
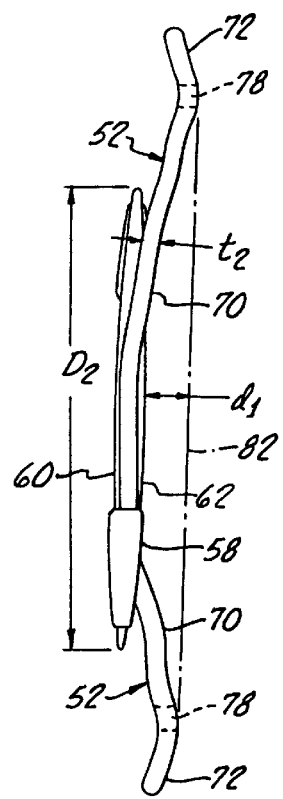
FIG. 3 is a side view of the IOL of FIG. 2, showing forward vaulting of the optic relative to the fixation loops.

Shown in FIGS. 2 and 3, comprising iris fixated IOL 20 are an optic 50 and a pair of opposing, similar and preferably identical, fixation members or haptics 52. Projecting sidewardly (radially) from opposite sides of a peripheral edge 56 of optic 50, and preferably formed in one piece with the optic, are similar structural haptic attachment abutments or bosses 58. Optic 50, which has respective anterior and posterior surfaces 60 and 62 (FIGS. 1 and 3), may be constructed as convex-convex (as depicted in FIG. 1), convex-concave, convex-planar, or concave-planar or concave-concave, all such and other configurations being within the scope of the present invention. Optic 50 may advantageously be provided in the diopter range between about −15 and about +15.

It is preferred that optic 50 be constructed from an elastically deformable material, such as a silicone or acrylic material, enabling the optic to be folded, rolled or otherwise deformed so that IOL 20 can be implanted through an ocular incision no larger than about 3.5 mm. It is therefore preferable that the material from which optic 50 is constructed have an index of refraction of at least about 1.46 and that the optic have a diameter, $D_2$, of between about 5.5 mm and about 7.0 mm (FIG. 3) and a center thickness, $t_1$, no greater than about 0.8 mm (FIG. 1).

Each of haptics 52, which are preferably constructed (as by micro-machining) from polymethyl methacrylate (PMMA), is formed having an arcuate, flexible proximal end region 70 and a generally flat, loop-shaped distal end region 72. A proximal end 74 of each haptic 52 is fixed into an associated one of bosses 58 (FIG. 2) so that haptic proximal end region 70 extends in a direction tangential to optic edge 56. Such haptic-to-optic fixation can be of any type used by IOL manufacturers for the secure attachment of haptics to soft, flexible optics.

Haptic proximal end region 70 is arcuate in plan view and arches away from optic 50 (FIG. 2). Further, proximal end region 70 is made flexible, particularly in a plane parallel to the plane of optic 50, by preferably having a width, $w_1$, of about 0.25 mm and a thickness, $t_2$ (FIG. 3) of about 0.35 mm. Preferably portions of haptic 52 defining distal end region loop 72 have about the same thickness as set forth for haptic proximal end region 70, and may be somewhat wider, as set forth below.

The loop into which haptic distal end region 72 is formed may be of a variety of shapes. However, the end region loop is shown in FIG. 2 as being elongated into a curved shape having a length, $l_1$ and flattened into a width, $w_2$. By way of example, with no limitation intended or implied, such loop length, $l_1$, may be about 3.0 mm and such loop width, $w_2$, may be about 1.0 mm.

A side region 76 of distal end region loop 72 that is closest to and directly faces optic 50 is formed defining an iris pincer gap 78 (FIG. 2) having a width, $w_3$, of about 0.1 mm and a length, $l_2$, of about 0.4 mm. Iris pincer gap 78 is shown oriented in a radial direction relative to a center 80 of optic 50, but may alternatively be oriented in another direction. As further, shown in FIG. 2, both iris pincer gaps 78 of the two haptics 52 are centered on a diameter, $D_3$, which is preferably about 8.5 mm. Pincer gaps 78 of both haptics 52 also lie generally on a common plane 82 (FIG. 3), the haptics being arched so that optic 50 is vaulted forwardly into anterior chamber 22 (FIG. 1) with posterior surface 62 anterior of plane 82 by a distance, $d_1$, that is preferably about 0.5 mm.

Overall diameter, of IOL 20 (to ends of haptics 52) is preferably between about 7.5 mm and about 10 mm so that the IOL haptics engage iris 14 at iris collarette region 32, as noted above (FIG. 1).

As a result of the flexibility of haptics 52, after one haptic has been attached to iris 14 by a pinching action (more particularly described below), optic center 80 can be easily aligned with optical axis 11 by flexing of the second haptic 52 before the second haptic is attached to the iris. Thus, centration of optic 50 on optical axis 11 of the eye is easily achieved.

Moreover, with optic 50 constructed from an elastically deformable material, IOL 20 can be implanted through a small ocular incision, as is important to minimize surgical trauma and possible complications, and reduce patient recovery time, all as compared to the surgical procedure required to implant a rigid iris fixation IOL. Further in this regard, the explanting of the flexible IOL 20, in the event explanting becomes necessary as the patient's vision changes with time, is also made easier.

From the foregoing, it will be appreciated that many variations to IOL 20 and particularly to haptics 52 which attach the IOL to iris 14 are possible and are to be considered as being covered by the present invention.

Figure 4:
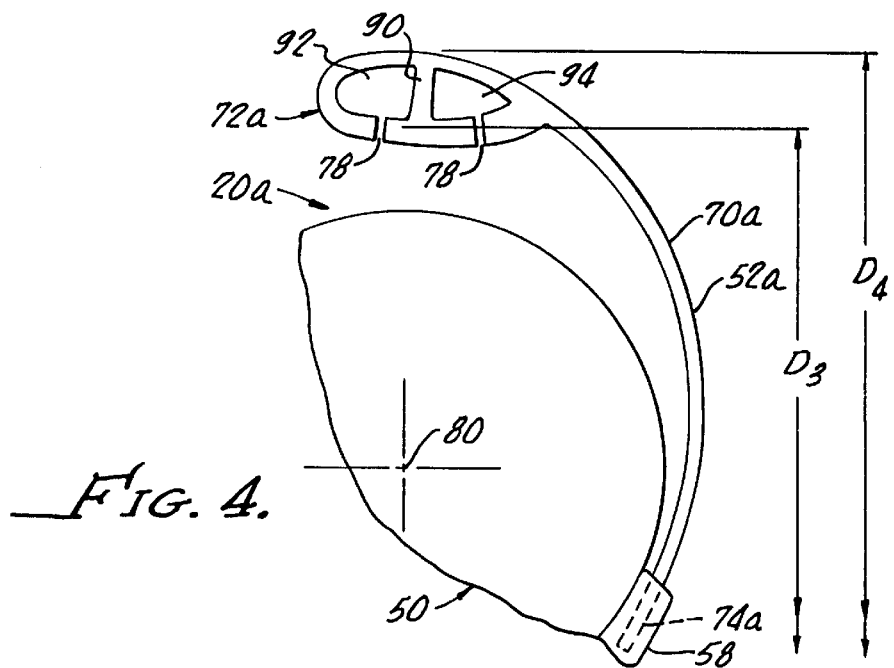
FIG. 4 is a partial front view of a variation fixation loop corresponding to the fixation loops shown in FIG. 2, showing a spaced apart pair of iris pincer gaps defined in the elongated vertically-divided fixation loop, both of such gaps shown directly facing the optic.

IOL VARIATION OF FIG. 4:

One of such variations is shown in FIG. 4 in connection with a variation IOL 20a, which is identical for descriptive purposes to above-described IOL 20 except as otherwise particularly described below. Corresponding elements and features are given the same reference numbers set forth above followed by an "a".

As shown, a looped distal end region 72a of a haptic 52a (corresponding to haptic 52) is divided radially (relative to center 80 of optic 50) by a narrow wall 90 into respective first and second loop sectors 92 and 94. Each such sector 92 and 94 is constructed to define an iris pincer gap 78 directly facing optic 50. Thus, each haptic 52a (only a representative one of which is shown) incorporates in distal end region 72a a spaced-apart pair of iris pincer gaps 78. This described doubling of the number of iris pincer gaps 78 in haptic loops 72a may sometimes be advantageous in securely detachably fixing IOL 20a to iris 14.

Figure 5:
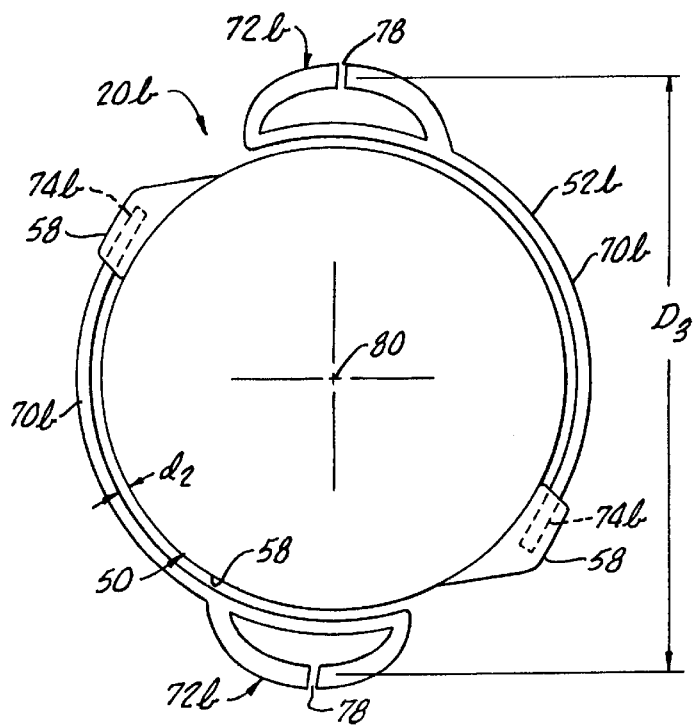
FIG. 5 is a front view of a variation three piece iris fixated IOL of the present invention, showing the optic and an opposing pair of haptics, each such haptic shown curving closely around the optic and terminating in an elongated fixation loop having a narrow, perpendicular pincer gap for enabling detachable attachment of the IOL to a patient's iris, the pincer gaps being shown facing away from the optic.
Figure 6:
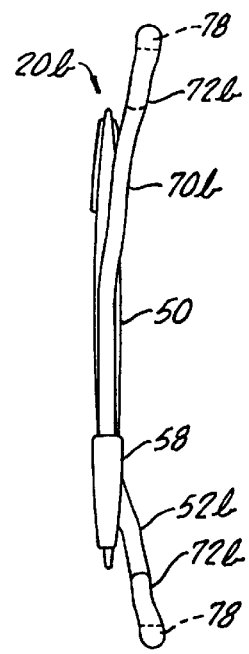
FIG. 6 is a side view of the IOL of FIG. 5, showing forward vaulting of the optic relative to the fixation loops.

IOL VARIATION OF FIGS. 5 AND 6:

Another such variation is shown in FIGS. 5 and 6 in connection with a variation iris fixation IOL 20b, which is identical for descriptive purposes to above-described IOL 20 except as otherwise particularly described below. Corresponding elements and features are given the same reference numbers set forth above followed by a "b".

A principal distinction between IOL 20b and above-described IOL 20 relates to pincer gaps 78 on haptic loops 72b facing away from optic 50 instead of directly facing the optic in the case of above-described IOL 20. Because pincer gaps 78 are spaced apart the same distance, $D_3$ (before disclosed in connection with IOL 20), proximal regions 70b of haptics 52b curve more closely around optic 50. Haptics 52b, are generally spaced from optic edge 56 a distance, $d_2$, that is at least about equal to a closest separation distance, $d_3$ (FIG. 1), between anterior surface 82 of natural lens 16 and posterior surface 84 of iris 14 (a distance typically of about 0.3 mm).

Since haptics 52b are otherwise similar to above-described haptics 52, this increased C-curvature of haptics 52b may provide somewhat increased haptic flexibility. Moreover, orienting pincer gaps 78 on haptic loops 72b away from optic 50 may, in some instances, facilitate fixation of the IOL to iris 14. The vaulting of optic 50 relative to haptic loops 72b is preferably the same as disclosed above relative to IOL 20.

Figure 7:
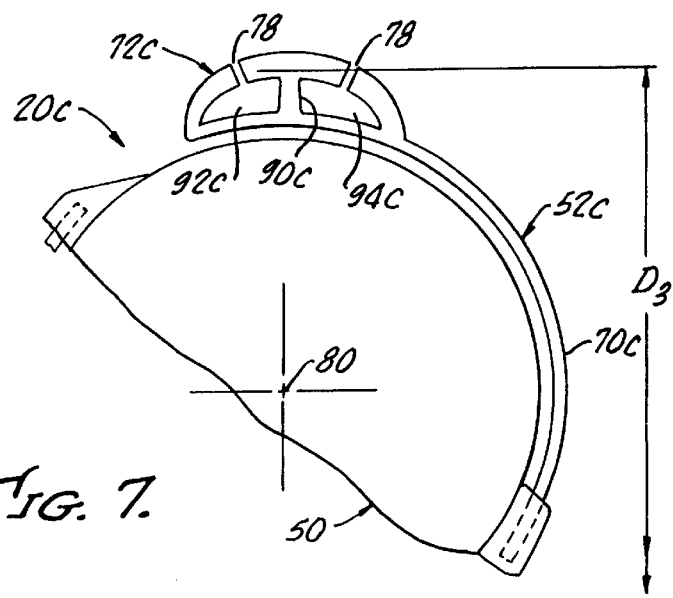
FIG. 7 is a partial front view of a variation fixation loop corresponding to the fixation loops shown in FIG. 5, showing a spaced apart pair of iris pincer gaps defined in the elongated vertically-divided fixation loop, both of such gaps shown directed away from the optic.

IOL VARIATION OF FIG. 7:

FIG. 7 depicts another variation iris fixated IOL 20c, which is identical for descriptive purposes to above-described IOL 20b except as otherwise particularly described below. Previously described features and elements are given the same reference number followed by a "c".

As can be seen, IOL 20c combines the described double pincer gap features shown for IOL 20a in FIG. 4 with IOL 20b (FIGS. 5 and 6.). Thus, as shown in FIG. 7, representative haptic loop 72c is vertically divided by a narrow wall 90c into first and second loop sectors 92c and 94c, respectively. Each sector 92c and 94c has defined a pincer gap 78 that faces away from associated optic 50.

Pincer gaps 78 on both haptic loops 72c (only one such loop being shown) are spaced a distance $D_3$ (defined above) apart.

Figure 8:
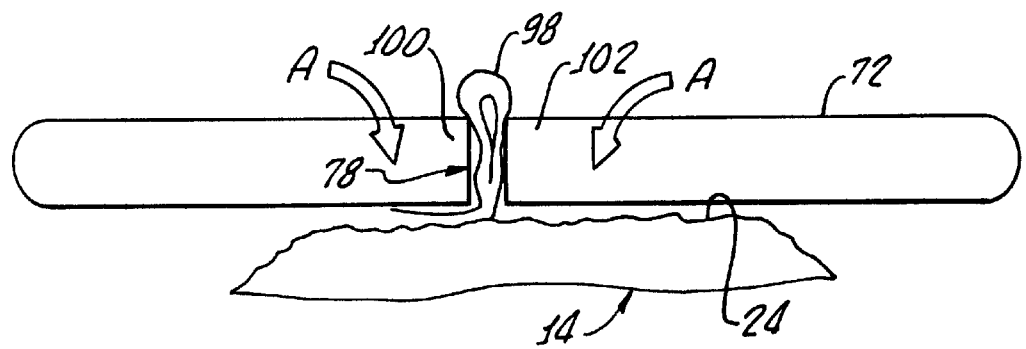
FIG. 8 is a drawing depicting the manner in which a representative right angle pincer gap, such as those shown in FIGS. 2, 4, 5 and 7, is operative for pinching an anterior surface region of an iris in a manner detachably attaching the associated fixation loop and thus the associated IOL to the iris.

OPERATION OF PINCER GAPS:

FIG. 8 depicts the manner in which a representative one of pincer gaps 78, on a representative haptic distal end region loop 72 pinches up a small surface segment 98 of iris tissue into the gap, thereby releasably or detachably fixing the associated haptic (e.g., haptic 52), and hence the associated IOL (e.g., IOL 20), to iris 14.

This pinching up of iris segment 98 is accomplished, foe example, by deflecting haptic loop regions 100 and 102 on each side of gap 78, downwardly (direction of Arrows "A") into iris surface 24. When the loop regions are released, they return to their original shape, thereby trapping iris segment 98 in gap 78.

VARIATION IRIS PINCER GAP OF FIG. 9:

It is to be understood that variations of the iris pincer gap may be made within the scope of the present invention and used in place of above-described pincer gap(s) 78. An example of such a variation is depicted in FIG. 9, in which a slanted iris pincer gap 78d (corresponding to above-described pincer gap 78) is depicted formed or defined in a representative haptic distal end region loop 72d (corresponding to above-described distal end region loop 72).

Figure 9:
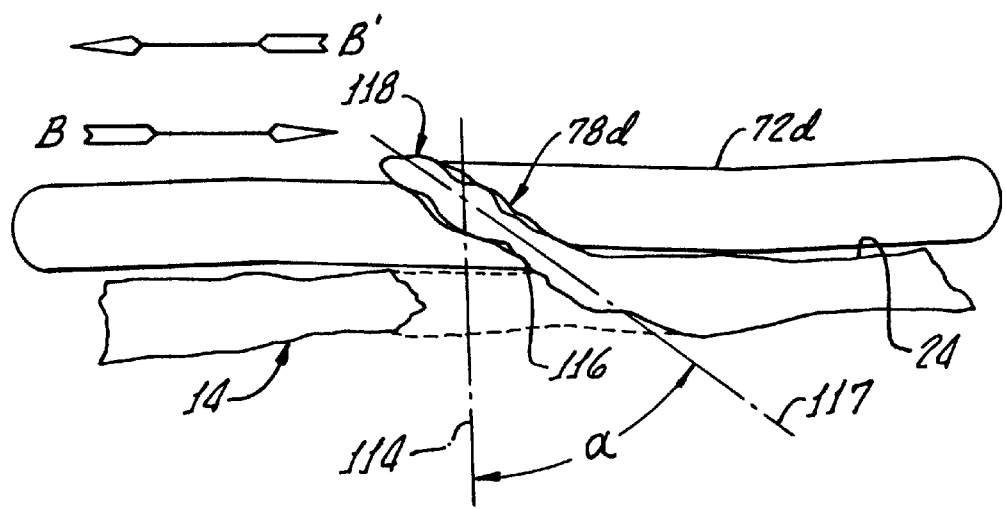
FIG. 9 is a drawing depicting the manner in which a representative angled pincer gap, corresponding to the right angle pincer gaps shown in FIGS. 2, 4, 5 and 7 is used to engage the anterior surface of an iris in a manner detachably attaching the associated fixation loop and thus the associated IOL to the iris.

Pincer gap 78d is depicted in FIG. 9 as formed or defined along a line 112 that is at an angle, $\alpha$, relative to a line 114 perpendicular to end region loop 72d. Preferably, slant angle, $\alpha$, is between about 30 degrees and about 60 degrees, with a slant angle of about 45 degrees being most preferred.

It is evident from FIG. 9 that when end region loop 72d is pressed against iris anterior surface 24 and is pushed or advanced in the direction indicated by Arrow "B", a sharp, leading lower edge 116 at gap 78d cuts into iris 14. This causes a small sliver 118 of iris 14 to be extruded into gap 78d, to thereby detachably fixate end region loop 72d, and hence associated haptic and IOL (neither shown in FIG. 9) to iris 14.

Distal end region loop 72d can be detached from iris by merely rotating the end region loop back in the direction indicated by Arrow "B".

PRIOR IOL IRIS FIXATION PROCESS OF FIGS. 10–11

Figure 10:
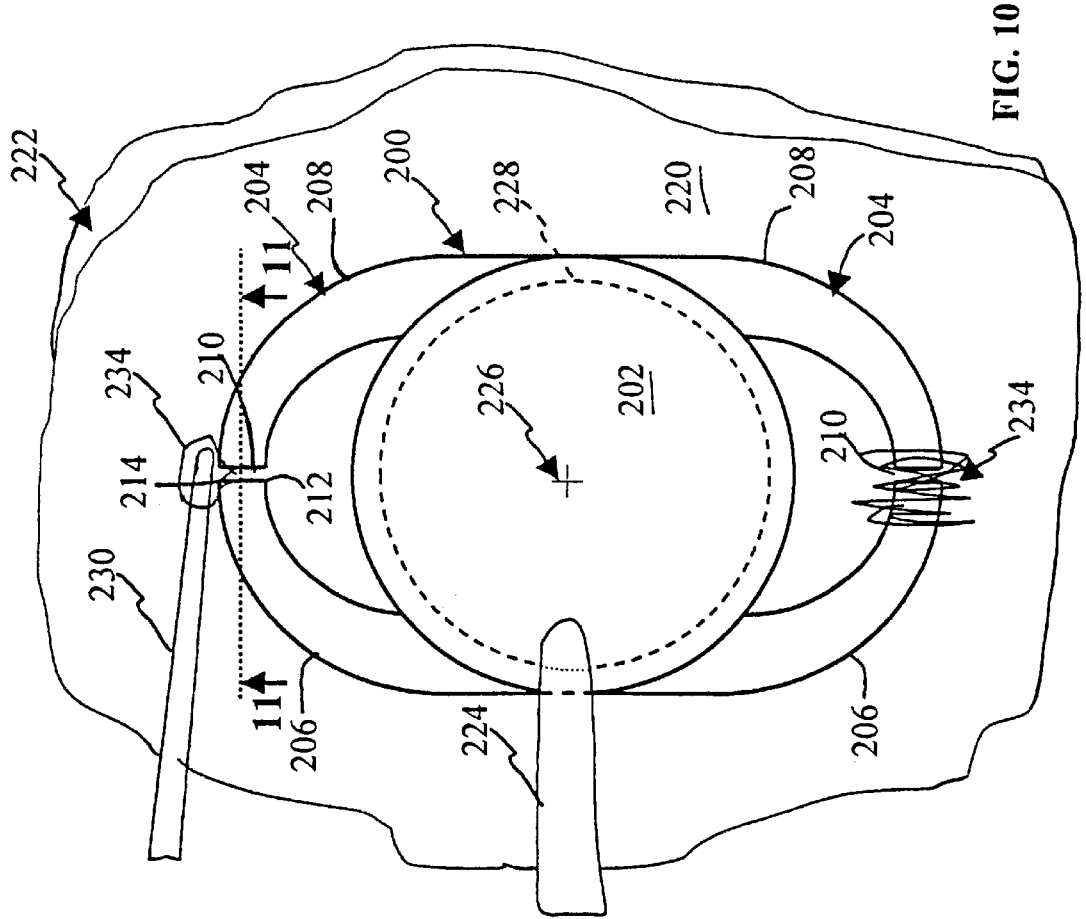
FIG. 10 is a plan view of a prior art iris fixated IOL illustrating the previously-used, two-handed iris attachment process involving the use by one hand (not shown) of forceps to hold the IOL in position against the anterior surface of the iris and simultaneously, involving the use by the other hand (also not shown), to manipulate a separate enclavation needle to engage (i.e.,pierce), with the needle tip, the anterior surface of the iris adjacent the upper pair of IOL fixation loop pincer arms and lift a small region of the iris tissue into the gap between the pincer arms.

There is depicted in FIG. 10, by way of example and for comparative purposes, an iris fixated IOL 200 of the general configuration disclosed in the above cited Worst patents.

Shown comprising IOL 200 are an optic 202 and an opposing pair (i.e., upper and lower, as depicted) of IOL fixation loops or members or haptics 204. Each fixation loop 204 comprises respective first and second pincer arms 206 and 208 that define a pincer gap 210 between opposing pincer arm end surfaces 212 and 214, respectively.

FIG. 10 further illustrates the heretofore-used (so far as is known to the present inventor) most commonly used procedure for attaching IOL 200 to an anterior surface 220 of iris 222, as has been briefly described in the foregoing BACKGROUND OF THE INVENTION.

As depicted, forceps, only a tip 224 of which is shown, are used by one hand (not shown) of the IOL implanting surgeon to grip an edge region of IOL optic 202. Forceps tip 224 hold IOL optic 202 in a manner holding IOL 200 against iris anterior surface 220 with optical axis 226 of the IOL optic aligned with the optical axis of pupil 228 (i.e., the optical axis of the eye).

With IOL 200 held and positioned in the above-described manner by forceps tip 224, an enclavation needle, only a tip region 230 of which is shown, is manipulated by the implanting surgeon's other hand (not shown) so that the needle tip pierces iris anterior surface 220 adjacent pincer gap 210 of one of the fixation loops 204—the uppermost fixation loop being depicted.

Figure 11A:
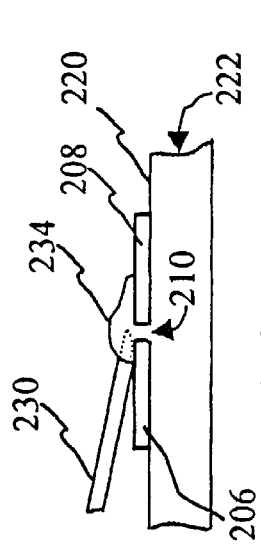
FIG. 11A showing a small region of iris issue adjacent the pincer arm gap engaged and lifted by the tip of the enclavation needle.

The needle is then manipulated so that needle tip portion 230 engages and starts lifting a small region 234 of iris stromal tissue, as also depicted in FIG. 11A.

Figure 11B:
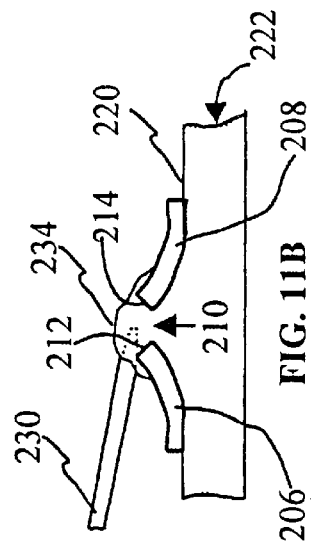
FIG. 11B showing the ends of the pincer arms adjacent the pincer arm gap, with opposing end regions of the pincer arms shown flexed upwardly and spread apart by the lifted tissue.

As depicted in FIG. 11B, with forceps tip 224 still holding IOL 200 properly positioned against iris anterior surface 220, needle tip portion 230 is then raised in a manner lifting engaged iris tissue region 234 into pincer gap 210. This tissue region 234 lifting process flexes end regions of pincer arms 206 and 208 upwardly, thereby widening pincer gap 210.

Figure 11C:
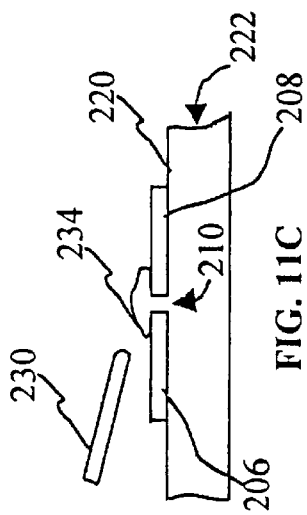
FIG. 11C showing the enclavation needle withdrawn from the iris tissue and opposing end regions of the pincer arms flexed back into their iris-attachment position, with a small region of iris tissue pinched in the pincer arm gap to thereby attach the pincer arms—and the associated IOL—to the iris.

Finally, as depicted in FIG. 11C, needle tip 230 is withdrawn from iris tissue region 234. Pincer arms 206 and 208 then flex back downwardly to their unflexed position (Ref. FIG. 11A), closing gap 210 and pinching iris tissue region 234 in the gap (as is also depicted for the lowermost fixation loop 204 of IOL 200 in FIG. 10).

Alternatively (not depicted), needle tip portion 230 may be used to depress an open end region of one of pincer arms 206 or 208 into iris anterior surface 220 such that when the pincer arm end region is released by needle tip region 230, some iris stromal tissue, corresponding to tissue region 234 is pinched in pincer arm gap 210.

The above-described iris tissue pinching in pincer gaps 210 of both fixation loops 204, detachably attaches IOL 200 to iris anterior surface 220. If detachment of IOL 200 from iris surface 220 later becomes necessary for any reason, the procedure described above is essentially reversed.

Although the above-described procedure for fixating IOL 200 to iris anterior surface 220 may appear relatively simple, in actual practice the procedure is one of the most difficult or all surgical procedures. This is because the procedure requires unusually great manual dexterity of both hands simultaneously.

COMBINATION FORCEPS AND ENCLAVATION NEEDLE INSTRUMENT

In order to reduce the currently great difficulty in performing the foregoing iris fixation surgical procedure and improve reproducibility of the fixation procedure, the present inventor has invented a combination forceps and enclavation needle instrument 300 (FIG. 12) that can be easily operated by one hand 302 as more particularly described below.

As shown, instrument 300 comprises an elongate operating head portion 304, an intermediate, operating head separation portion or means 305 and an elongate, preferably cylindrical, handle or barrel portion 306. Operating head portion 304 includes a tubular, ocular insertion member 308 which, with separation portion or means 305 extends from a distal end 310 of handle or barrel portion 306 along a longitudinal axis 312 of the instrument.

Handle portion 306 may advantageously be constructed of two longitudinal half sections (not individually shown) attached together by two screws 314 to enable internal access for assembly, maintenance and any required repair.

Projecting from an open, distal end 314 of operating head portion 304 are a forceps tip 322 and an enclavation needle tip 324, also as more particularly described below.

With no limitations being intended or implied, a tubular insertion member 308 of operating head portion 304 may have a length, $l_3$, of about 8 mm. Insertion member 308 is preferably elliptical or oval in transverse cross section, having a major cross sectional dimension, $a_1$, of no more than about 2.5 mm and a minor cross sectional dimension, $a_2$, of no more than about 1.9 mm (see FIG. 13) to enable its insertion through a small ocular incision. An overall length, $l_4$, of operating head portion 304 may be about 40 mm.

Without limitation, handle portion 306 may have a length, $l_5$, of about 170 mm, and is preferably round with an outside diameter, $D_7$, of about 25 mm.

Installed in handle portion 306 are needle and forceps tip operating and control system or means 328 which is preferably electrical powered, as more particularly described below. System 328 is configured for enabling forceps tip 322 and enclavation needle tip 324 to be operated by one user hand 302 to detachably attach (and/or remove) an iris fixated IOL, similar to IOL 20 (FIG. 2) in a manner similar to that described above for IOL 200 (FIGS. 10–11).

Figure 12:
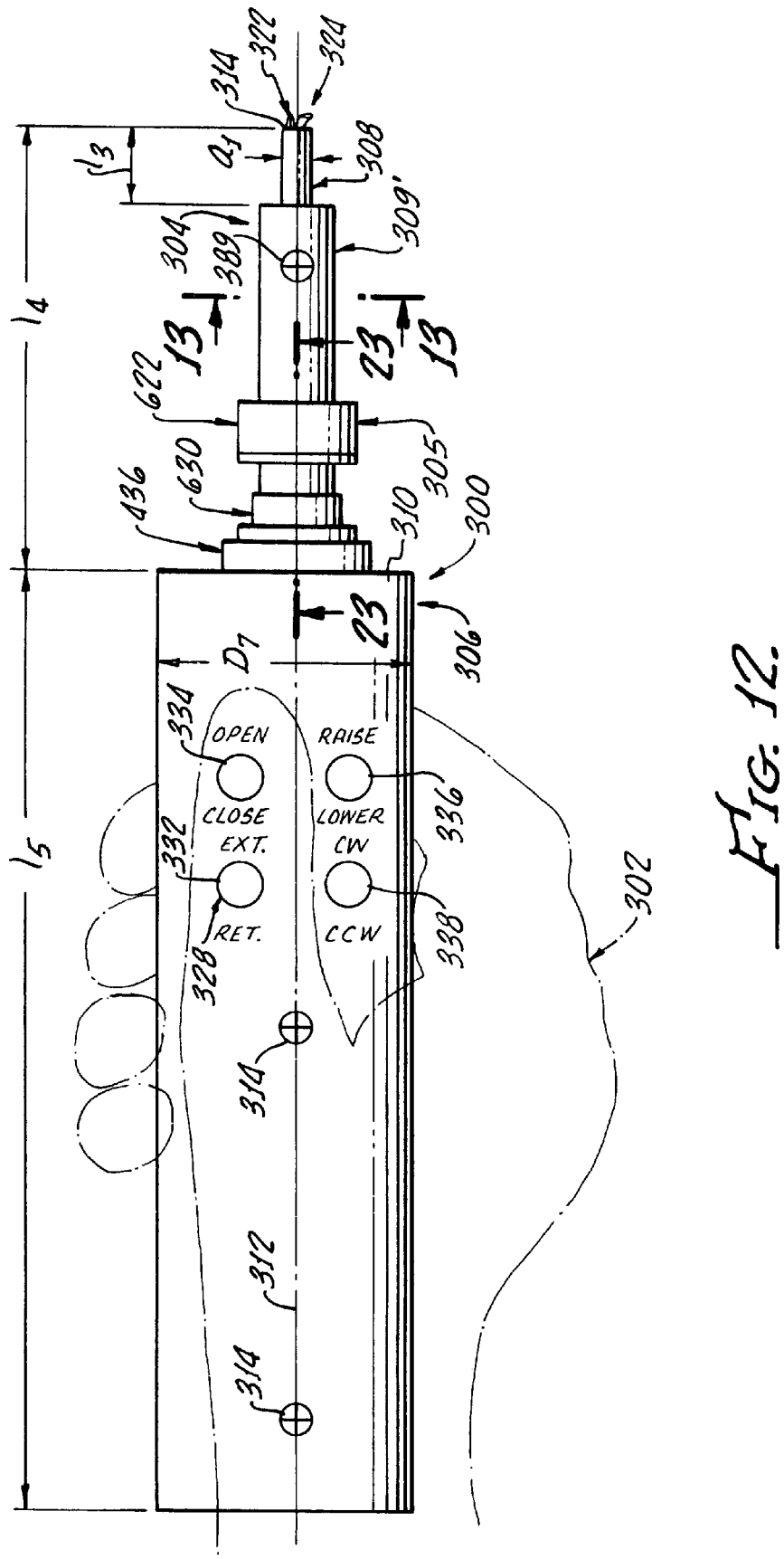
FIG. 12 is a perspective drawing of a combination forceps and enclavation needle instrument in accordance with the present invention useful for attaching an iris fixated IOL to the anterior surface of a patient's iris, showing a forceps tip and needle tip projecting from a slender operating head portion of the instrument and showing external elements in a handle portion of the instrument for enabling the manipulation of the forceps and needle tips by one hand of a user.

Also shown in FIG. 12 comprising externally accessible portions of operating and control system 328 are respective first, second, third and fourth momentary-on/off/ momentary-on electrical switches 332, 334, 336 and 338 by which forceps tip 322 and needle tip 324 can be micro-manipulated by the user's one hand 302.

As more particularly described below, first switch 332 is electrically connected for selectively moving both forceps tip 322 and needle tip portion 324 in extended and retracted axial directions a limited adjustment distance of several mm. Second switch 334 is electrically connected for selectively opening and closing forceps tip 322. Third switch 336 is electrically connected for selectively raising and lowering needle tip 324. Fourth switch 338 is electrically connected for simultaneously partially rotating needle tip 324 in clockwise (CW) and counterclockwise (CCW) directions with associated extending and retracting of the needle tip for helical needle tips, as described below.

Figure 13:
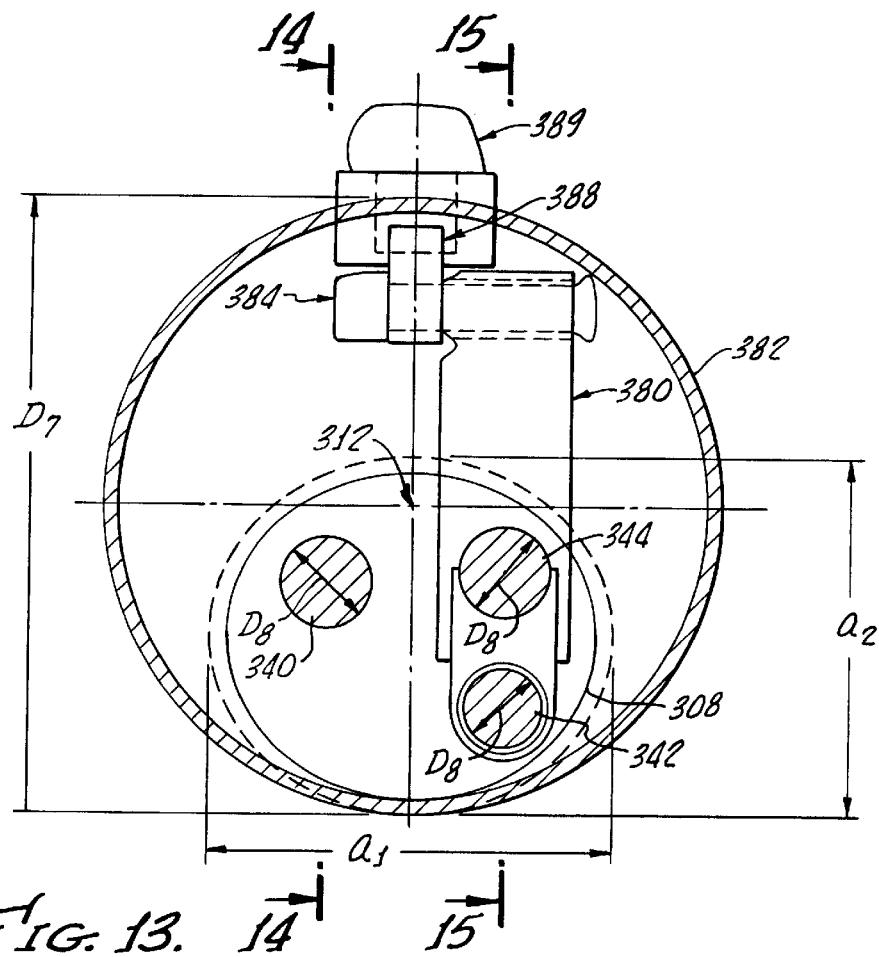
FIG. 13 is a transverse cross sectional drawing looking along line 13—13 of FIG. 12, showing three operating rods of a forceps tip and needle tip operating and control system.

FIG. 13 is a transverse cross sectional drawing of insertion member 308 showing a rod or pin 340 for operating forceps tip 322 and rods or pins 342 and 344 for operating needle tip 324. Rods or pins 340, 342 and 344 preferably each have a cross sectional diameter, $D_8$, which is about 0.5 mm.

Figure 14:
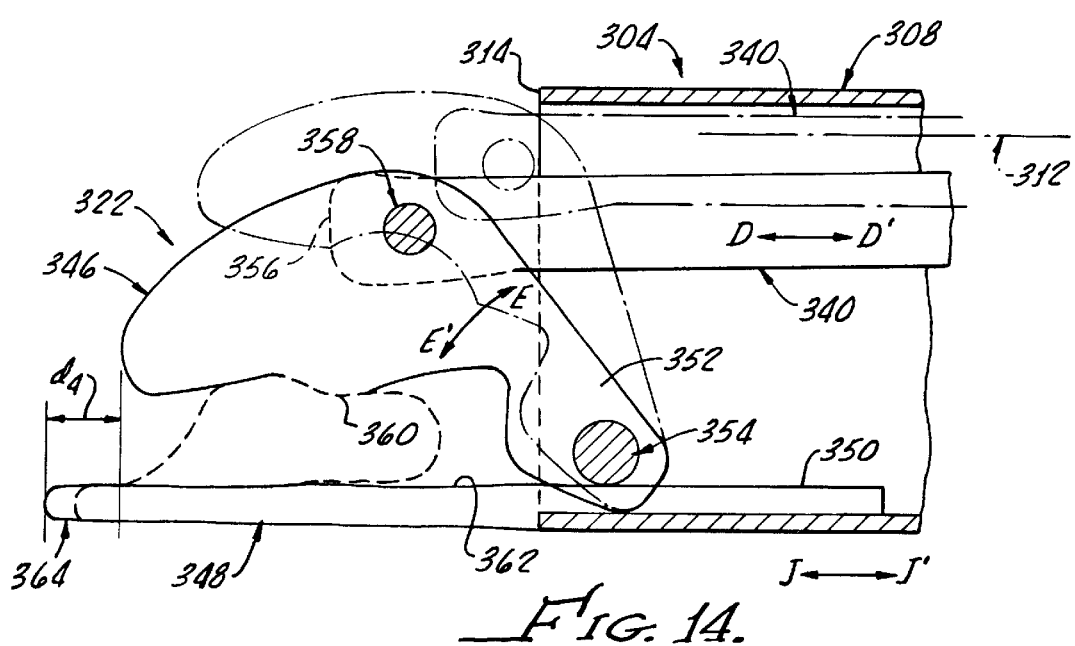
FIG. 14 is a longitudinal cross sectional drawing looking along line 14—14 of FIG. 13, showing details of the forceps tip portion of the combination instrument depicted in FIG. 12, showing upper and lower jaws of the forceps tip in both the closed and open positions, the closed position showing the forceps tip (in solid lines) gripping a portion of the IOL fixation loop (shown in broken lines) and the open forceps tip position being shown dotted lines, and further showing pivotal mounting of a lower region of the upper jaw to the instrument tip and showing an operating pin pivotally attached to a mid region of the upper jaw.

As more particularly shown in FIG. 14, forceps tip 322 projects axially beyond open end 314 of instrument operating head insertion member 308. It should be noted that the term "forceps tip" is used herein in conjunction with reference number 322 to enable a direct comparison with above-described forceps tip 234 (FIG. 10), even though the described forceps tip 322 does not actually resemble the tip of a conventional forceps.

Shown comprising forceps tip 322 are respective upper and lower gripping jaws 346 and 348. Lower jaw 348 is substantially flat and is directed parallel to handle axis 312, having a rearward end region 350 fixed to a lower region of tubular insertion member 308.

Forceps tip upper jaw 346 is generally C-shaped and has a lower end region 352 pivotally mounted, by a pivot pin 354, to a lower region of member 308. A distal end 356 of forceps control rod or pin 340 is pivotally attached, by a pivot pin 358, to an upper, central region of upper jaw 346.

When control rod 340 is moved in an axial direction away from forceps tip upper jaw 346 (direction of Arrow "D", FIG. 14) by switch 334 (FIGS. 12 and 16) of operating and control system 328, the upper jaw is pivoted upwardly (direction of Arrow "E") about pivot pin 354 to or toward the fully-open position indicated by phantom lines.

In contrast, when forceps tip control rod or pin 340 is caused to be moved in an axial direction toward upper jaw 346 (direction of Arrow "D'", FIG. 14) by operating and control system switch 334, the upper jaw (if open) is pivoted downwardly (direction of Arrow "E'") about pivot pin 354 to or toward its closed position (shown in solid lines).

This described opening and closing movement of upper jaw 346 enables forceps tip 322 to grip an IOL fixation loop region 360 (depicted in phantom lines in FIG. 14) that is supported on an upper surface 362 of forceps tip lower jaw 348 (also as more particularly described below).

As shown, a free, distal end 364 of lower jaw 348 extends a distance, $d_4$, of about 0.20 mm beyond upper jaw 346 for facility of operation, as described below.

Figure 15:
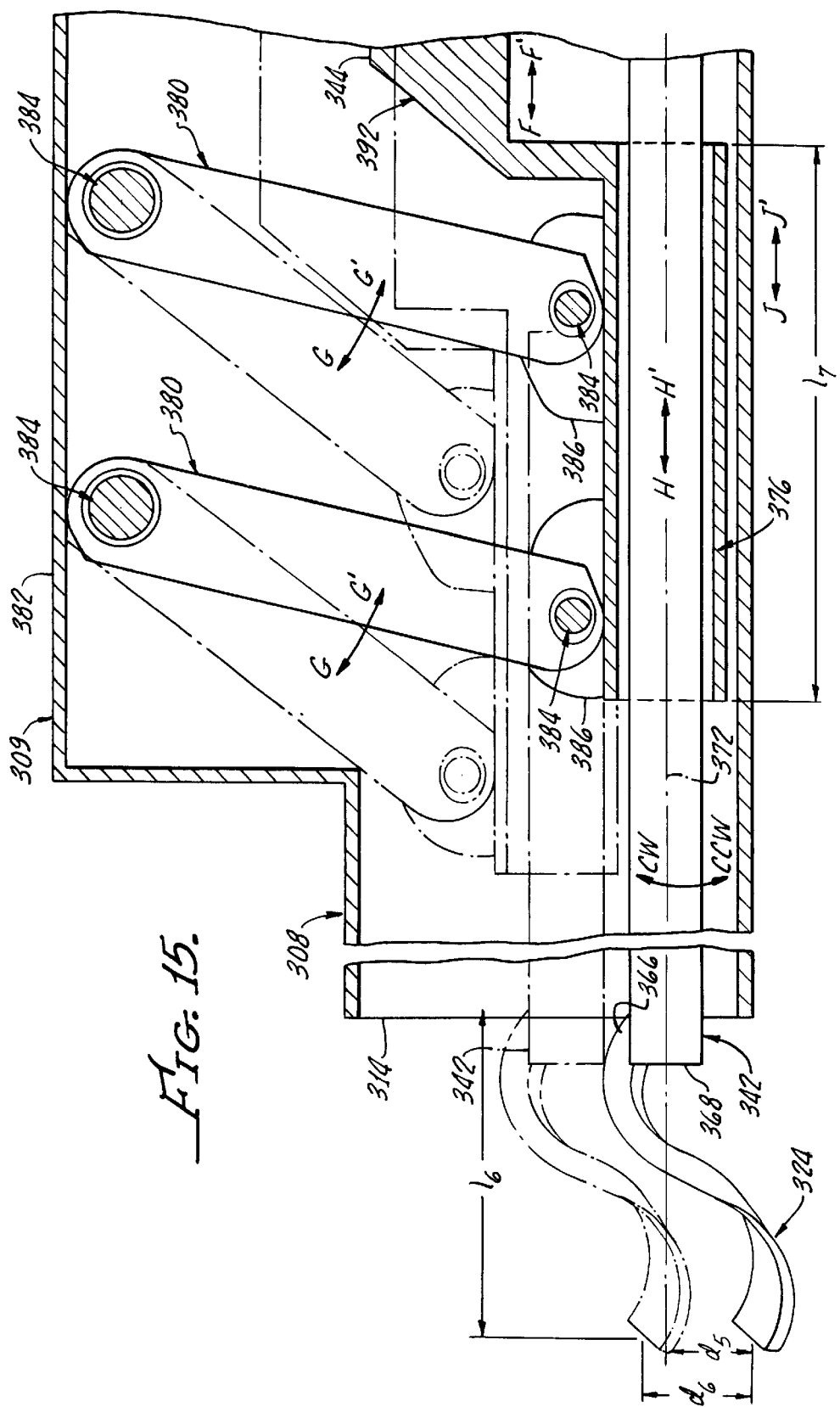
FIG. 15 is a longitudinal cross sectional drawing looking along line 15—15 of FIG. 13, showing details of the enclavation needle tip portion of the combination instrument depicted in FIG. 12, showing in solid lines an exemplary, or spiral enclavation needle tip in its lowered position and showing in phantom lines the needle tip in its raised position, and further showing the mechanism by which the needle is raised and lowered.
Figure 18A:
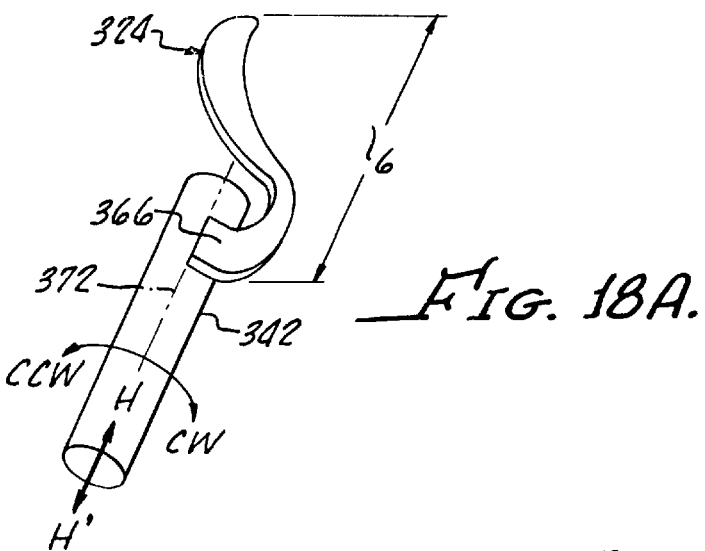
FIG. 18A depicting an offset, axial, helical needle tip.

As shown in FIG. 15, a proximal end 366 of needle tip 324 that projects beyond open end 314 of insertion member 308 is attached in an offset manner (as depicted in FIG. 18A) to a distal end region 368 of needle tip control rod or pin 342.

By way of specific example, with no limitation thereby intended or implied, needle tip 324 preferably has a length, $l_6$, of about 1.0 mm, and has a helical or "corkscrew" shape in a longitudinal direction. Needle tip 324 is preferably offset a distance, $d_5$, of about 0.9 mm from a longitudinal axis 372 of control rod 342 (see also FIG. 18A).

Needle tip control rod 342 is loosely or slidably disposed through a short axial tubular member 376, having a length, $l_7$, of about 10 mm. Tubular member 376 is pivotally connected by an axially-separated pair of links 380 to a proximal insertion member region 382 having a diameter, $D_9$, of about 10 mm (FIG. 13). Links 380 are shown pivotally mounted at each end by pivot pins 384 to respective inner and outer brackets 386 and 388 (FIG. 13) fixed respectively to tubular member 376 and insertion member region 382. Outer brackets 388 are detachably attached to outer member region 382 by screws 389 (FIG. 13).

The proximal end region of tubular member 376 is connected by an offsetting element 392 to a distal end of control rod or pin 344. It can thus be seen from FIG. 15 that when control rod or pin 344 connected to tubular member 376 is caused to be moved axially toward needle tip 324 (direction of Arrow "F'") by switch 336 of operating and control system 328, links 380 are caused to pivot upwardly (direction of Arrow "G"). Such upward pivoting of links 380 lifts or pulls up tubular member 376 with its enclosed needle tip control rod or pin 342 and attached needle tip 324 a distance, $d_6$, of about 0.7 mm to an needle tip iris tissue lifting position (shown in broken lines).

In a reverse action, when control rod or pin 344 attached to inner tubular member 376 is caused to be moved axially away from needle tip 324 (direction of Arrow "F'") by switch 336, links 380 are caused to pivot back downwardly (direction of Arrow "G'"). Such downward pivoting motion of links 380 causes the lowering of needle tip control rod or pin 342 and attached needle tip 324, to or toward the tissue-penetrating needle tip position shown in solid lines.

It is to be appreciated that needle tip rod or pin 342 remains free to rotate and move axially within tubular member 376. Thus, rod or pin 342 and attached needle tip 324 connected thereto can, during the iris fixation of an iris fixated IOL, rotated in either the clockwise (CW) direction or the counterclockwise (CCW) direction and moved axially (in the direction of Arrow "H" or "H'") in tubular member 376 by operating and control system switch 338 (FIGS. 12 and 16).

Forceps tip 322 and needle tip 324 can also be selectively moved, in unison, in a forward, extending direction (direction of Arrow "J") or a rearward, retracting direction (direction of Arrow "J'") with insertion member 308 by operating and control system switch 332 (FIGS. 12 and 16), as more particularly described below. Such extension/ retraction axial movement of forceps tip 322 and needle tip 324 enables an operator of instrument 300 to adjust the axial positional of the tips as may be desired or needed for accurate fixation position of an iris fixated IOL.

Figure 16:
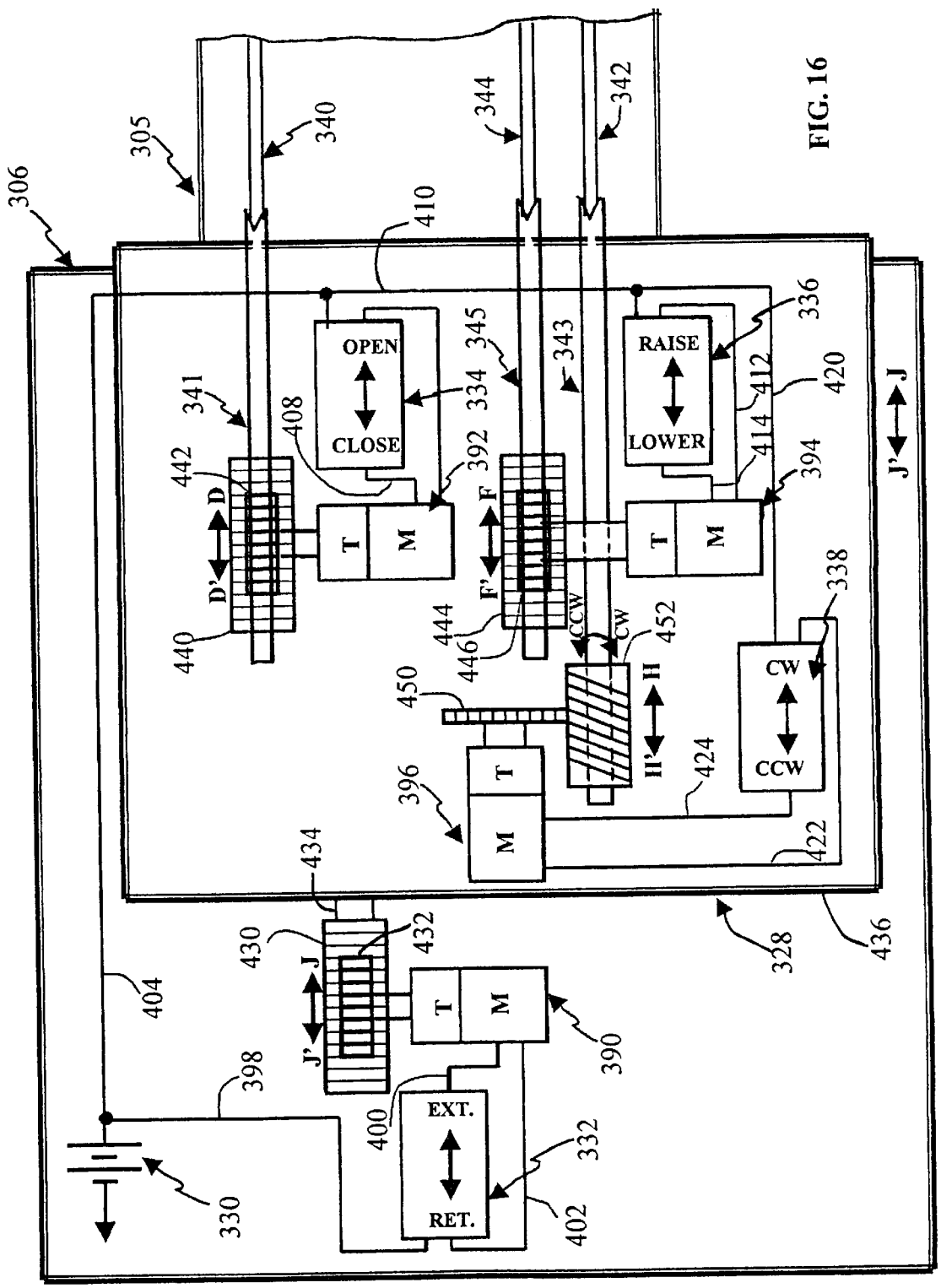
FIG. 16 is a schematic drawing showing electrical implementation of the operating and control system of the combination forceps and enclavation needle instrument depicted in FIG. 12, showing four rotational or advancing/retracting miniature, reversing electrical motors and associated gears, and showing associated electrical switches for selective operation of the motors.

Shown in the electrical schematic drawing of FIG. 16 further comprising operating and control system 328, in addition to previously-mentioned switches 332–338 and battery 330 (which may be a conventional 1.5 volt battery), are respective first, second, third and fourth combination reversible motors and reduction gears (transmissions) 390, 392, 394 and 396.

Forceps tip and needle tip extension and retraction control switch 332 is shown connected to battery 330 by a wire 398 and by electrical wires 400 and 402 to motor and transmission 390 to cause forward and reverse operation of the motor.

In a similar manner, forceps tip opening and closing control switch 334 is connected to battery 330 by a wire 404 and by electrical wires 406 and 408 to motor and transmission 392 to cause forward and reverse operation of the motor.

Needle tip raising and lowering switch 336 is, in turn, shown connected to battery 330 by wires 404 and 410 and by electrical wires 412 and 414 to motor and transmission 394 to cause forward and reverse operation of the motor.

Finally, needle tip rotational and axial movement control switch 338 is shown connected to battery 330 by a wire 420 and by electrical wires 422 and 424 to motor and transmission 396 to cause forward and reverse operation of the motor.

Forceps tip and needle tip motor and transmission 390 is connected, through respective rack and pinion gears 430 and 432 and a drive rod 434 to an axially movable, internal, motor and switch housing 436. In turn, internal housing 436 is connected, through separation portion 305 to insertion member 308 (not shown in FIG. 16), to thereby enable selective forward or rearward movement of forceps tip 322 and needle tip 324 in unison (as described above), by operation of switch 332.

Forceps tip motor and transmission 392 is connected, through respective rack and pinion gears 440 and 442 to a forceps tip connector pin or rod 341, that is detachably connected to forceps tip control pin or rod 340, to thereby enable selective opening and closing of forceps tip 322 (as described above), by operation of switch 334.

In turn, needle tip motor and transmission 394 is connected, through respective rack and pinion gears 444 and 446 to a needle tip tubular member connector pin or rod control rod or pin 345, that is detachably connected to needle tip raising/lowering control pin or rod 344, to thereby enable raising and lowering of needle tip 324 (as described above), by operation of switch 336.

Finally, needle tip rotation and axial movement motor and transmission 396 is connected, through respective worm gears 450 and 452 to a needle tip connector pin or rod 343, that is detachably connected to needle tip control pin or rod 342. Worm gears 450 and 452 are configured for enabling simultaneous CW and limited axial outward movement or CCW rotation and simultaneous axial inward movement of needle tip 324 (as described above), by operation of switch 338.

As shown in FIG. 16, all components of operating and control system 328, except battery 330, switch 322 and associated motor and transmission 390, gears 430 and 432 and rod 434, are installed in internal housing 436 so as to move axially therewith by operation of switch 332.

Figure 17:
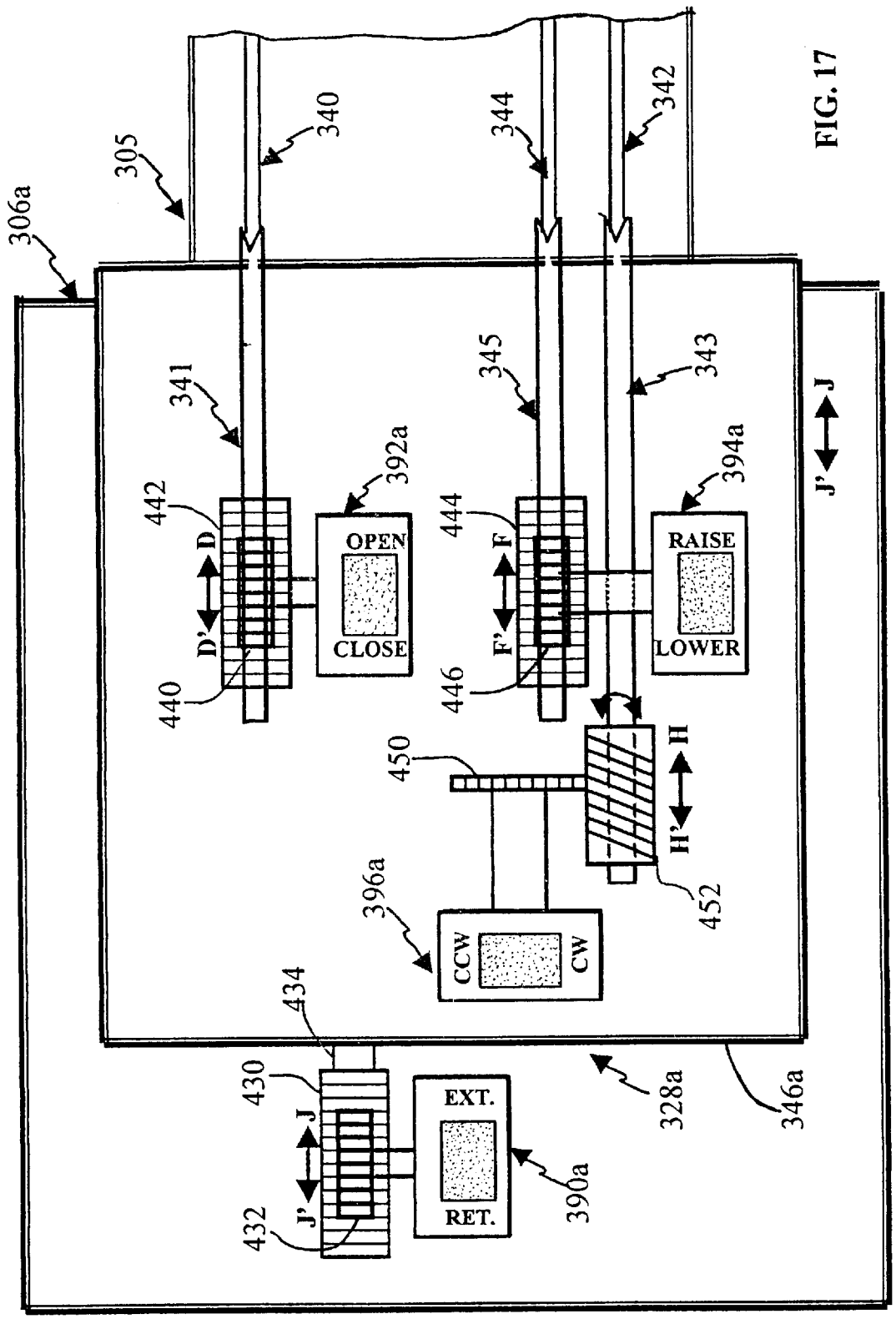
FIG. 17 is a schematic drawing of a variation operation and control system that is the mechanical equivalent of the electrical operating and control system depicted in FIG. 16, four thumb-wheels being shown substituted for the four reversible motors and associated electrical switches.

Although, electrical operating and control system 328 described above relative to FIG. 16 will ordinarily be preferred for ease of precise operation of forceps tip 322 and needle tip 324, FIG. 17 depicts a non-electrical (i.e., entirely mechanical) variation operating and control system 328a. System 328a is in all respects the mechanical equivalent of electrical operating and control system 328 and may, for some situations, be preferred.

In mechanical system 328a, that is installed in an instrument handle portion 306a, a thumb-wheel 390a replaces or is used in lieu of needle tip and forceps tip extension and motor and transmission 390 and switch 332 of system 330. A thumb-wheel 392a replaces or is used in lieu of forceps tip opening and closing motor and transmission 392 and switch 334. A thumb-wheel 394a replaces or is used in lieu of needle tip raising and lowering motor and transmission 394 and switch 336. A thumb-wheel 396a replaces or is used in lieu of needle tip rotation motor and transmission 396 and switch 338. Thumb-wheels 390a, 392a, 394a and 396a project through handle portion 306a for operational purposes.

In mechanical operating and control system 328a, battery 330 and all associated electrical wiring depicted in FIG. 16 for electrical operating and control system 330 are, of course, eliminated.

FIG. 18 depicts, for illustrative purposes, with no limitation being thereby intended or implied, several variations of enclavation needle tip configurations that the present inventor has determined may be useful in conjunction with instrument 300 for engaging iris tissue and lifting the engaged iris tissue into pincer gap 490. FIG. 18A shows above-described axial helical needle tip 324 as having the above-described length, $l_6$, of about 1 mm and as having a sidewardly offset distance, $d_7$, from control rod longitudinal axis 372 of about 0.4 mm.

Figure 18B:
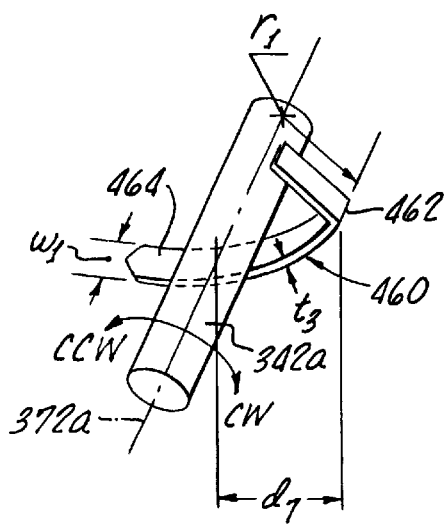
FIG. 18B depicting an arcuate, sidewardly-extending offset needle tip.

FIG. 18B shows a first variation, arcuate needle tip 460 that has a radius of curvature, $r_1$, equal to about 0.9 mm, and that is curved through about 900. Needle tip 460 has a generally uniform width, $w_4$, of about 0.3 mm and tapers from a thickness, $t_3$, of about 0.15 mm at an attachment end 462, to a knife-edge at a free, pointed end 464. Tip attachment end 462 is offset in a horizontal direction from needle tip control rod longitudinal axis 372a the distance, $d_7$, (i.e., about 0.4 mm).

Figure 18C:
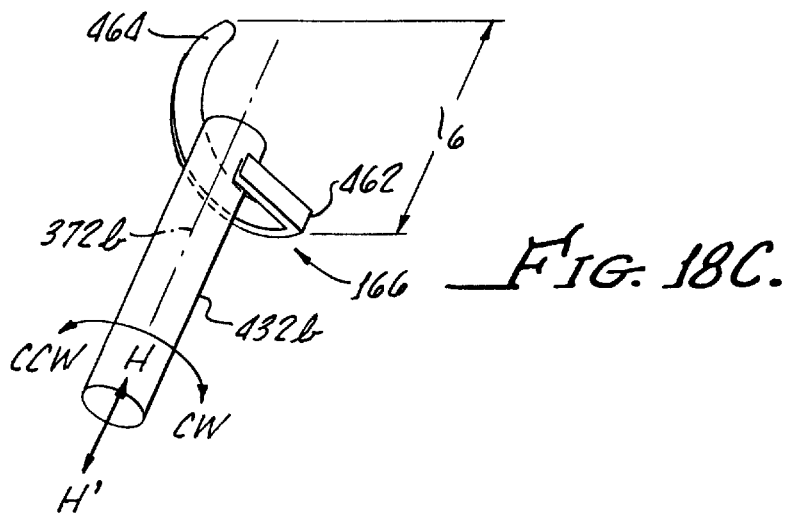
FIG. 18C depicting a forwardly directed, spiral needle tip similar to the needle tip depicted in FIG. 18A.

Shown in FIG. 18C is a second variation needle tip 466 that is similar in some respects to both needle tips 324 and 460 (FIGS. 18A and 18B). Needle tip 466, which is curved similar to needle tip 460, spirals forwardly in a manner similar to helical needle tip 324.

All of needle tips 324, 460 and 466, as well as all variations thereof, are preferably constructed from surgical-grade stainless steel or other strong, biocompatible material and may utilize diamond tips for optimum wear characteristics.

It is important to note that for needle tips 324 (FIG. 18A) and 466 (FIG. 18C) associated gears 450 and 452 (FIGS. 16 and 17) are configured for causing simultaneous needle tip rotational movement and axial movement. For needle tip 460 (FIG. 18B) and other, comparable needle tips-not illustrated), gears 450 and 452 are configured for providing only needle tip rotational movement.

IOL FIXATION LOOP SPECIFIC CONFIGURATION OF FIGS. 19–21:

The present inventor has further determined that advantages can be obtained by specifically configuring, as shown in FIGS. 19–21, an IOL fixation loop 478 of a variation iris fixated IOL 480 (similar to iris fixated IOL 20, FIG. 2) to cooperate with operation of above-described combination forceps tip and needle tip instrument 300 (again, as more particularly described below).

Fixation loop 478 corresponds generally to fixation loop 72 depicted in FIG. 2 and described above. As such, fixation loop 478 is formed having respective first and second pincer arms 482 and 484. Respective adjacent ends 486 and 488 of pincer arms 482 and 484 define therebetween a narrow pincer gap 490 (corresponding to above-described pincer gap 78, FIG. 2) preferably having a gap width, $w_5$, of about 0.07 mm.

As depicted in FIG. 21, pincer arm 482, which is representative of pincer 484, is substantially flat and rectangular with rounded corners, having a preferred width, $w_6$, of about 0.35 mm and a preferred thickness, $t_4$, of about 0.15 mm. A fixation loop side region 492 opposite pincer gap 490 is preferably round in cross section, having a diameter, $D_{10}$, of about 0.2 mm.

As shown in FIG. 20, respective lower surfaces 500 and 502 of fixation loop opposite end regions 504 and 506 are flared or offset upwardly a preferred distance, $d_8$, of about 0.15 mm above a plane 510 defined by respective lower surfaces 512 and 514 of pincer arms 482 and 484. Note that plane 510 is also coincident with an iris anterior surface (such as iris surface 220, FIG. 10) when IOL 480 is fixated to an iris. Such upward offset of end regions 504 and 506 provides clearance for forceps tip lower jaw 348 (FIG. 14), as described below.

Respective target gripping regions 520 and 522 of fixation loop end regions 504 and 506 are preferably thickened by a distance, $d_9$, of about 0.1 mm (FIG. 21). These regions 520 and 522 not only provide thickened regions for right angle gripping by forceps tip 322 during iris fixation of loop 478 (as shown in FIG. 22), but also provide visual guides for enabling accurate right angle positioning of the forceps tip.

OPERATION OF INSTRUMENT 300—FIG. 22

Figure 22B:
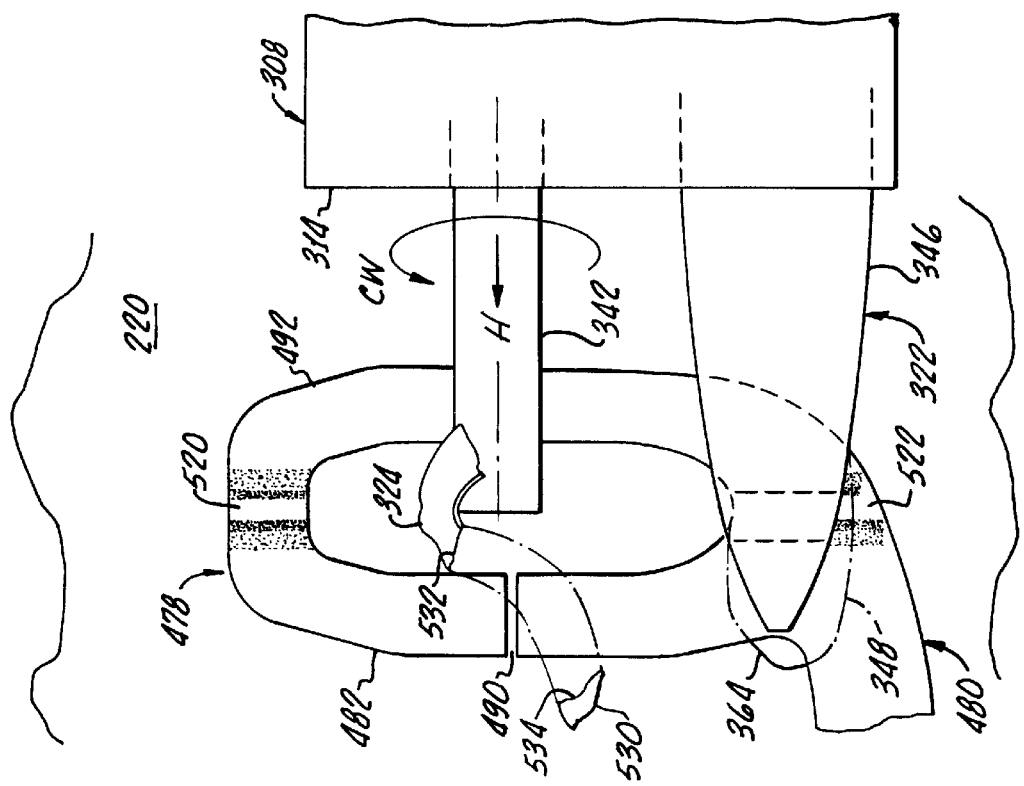
FIG. 22B showing the forceps tip still holding the fixation loop against the iris surface and depicting the helical needle tip advanced in the direction of Arrow "E" and partially rotated in the CCW direction to insert the needle tip beneath the iris surface diagonally under the pincer arm gap.
Figure 22A:
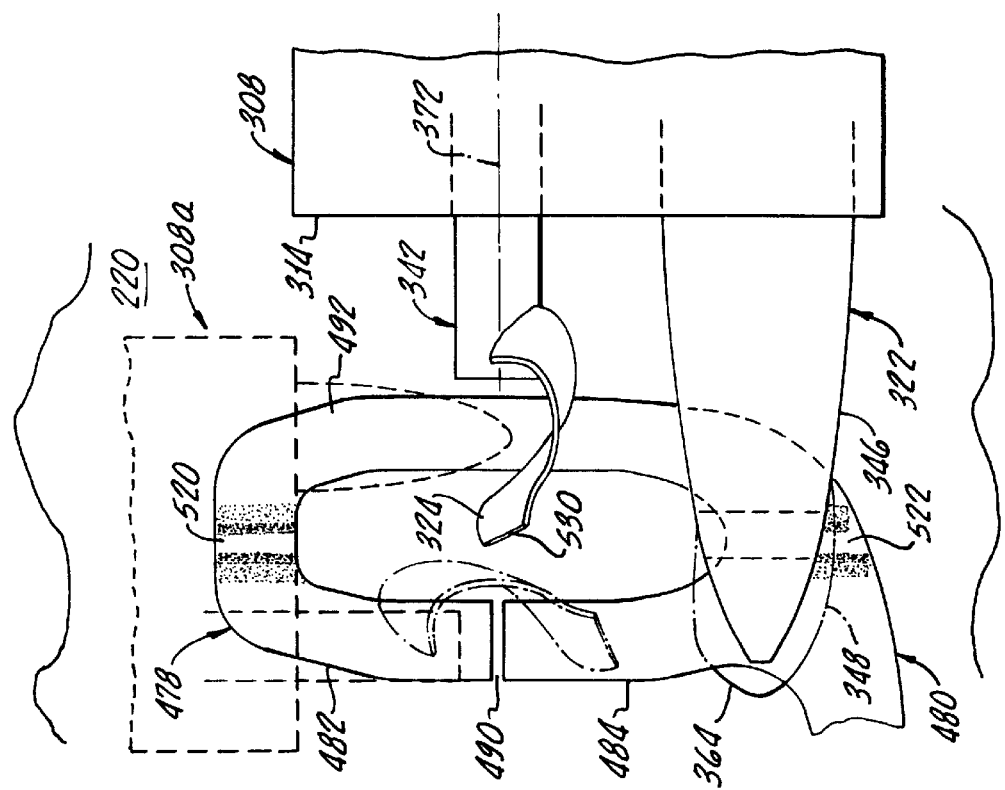
FIG. 22A depicting the forceps tip gripping one of the thickened end regions of the fixation loop to hold the fixation loop against the anterior surface of an iris and with the enclavation needle tip portion positioned above the iris surface inside the fixation loop near the fixation loop pincer arm gap and showing in broken lines an alternative positioning of the forceps tip and needle tip.

FIG. 22 depicts, in a series of four steps, typical operation of combination forceps and enclavation needle instrument 300 in combination with fixation loop 478 of exemplary iris fixated IOL 480. By way of example, instrument insertion member 308 is shown in FIGS. 22A–D in solid lines positioned at a right angle to the long axis of fixation loop 478; however, there is indicated by broken lines in FIG. 22A an alternative positioning of the instrument member designated 308a parallel to the long axis of the fixation loop.

For purposes of describing the fixation loop attachment procedure, with no limitation being thereby intended or implied, electrical operation and control system 328 is assumed.

IOL 480 is first inserted, using known IOL insertion procedures, through an ocular incision (not shown) into the anterior chamber of a patient's eye. Forceps tip 322 and needle tip 324 are then optimally positioned relative to a selected fixation loop 478 (for example, with the aid of visual optics) by the ophthalmic surgeon's manipulation of operating and control switch 332 as described above with respect to FIGS. 12 and 16). As described above with respect to FIGS. 12 and 16, needle tip 324 is elevated by the surgeon to the desired elevation by manipulation of switch 336 and forceps tip 322 is opened by manipulation of switch 334.

Then, as depicted in FIG. 22A by way of example, forceps tip lower jaw 348 is moved into a position beneath raised region 522 of fixation loop 478. Accurate positioning of forceps tip 322 is visually determined by visually observing when lower jaw end 364 becomes visible beyond fixation loop 478 in the region of pincer arm 484, with the loop resting on lower jaw upper surface 362 (see FIG. 14). Switch 334 is then manipulated to close forceps tip upper jaw 346 against fixation loop region 522 (see also FIG. 14).

Needle tip 324 is configured so that at the above-described fixation loop gripping position of forceps tip 322, a sharp needle tip distal end 530 is positioned above a desired iris tissue engagement point within fixation loop 478 and adjacent to and in alignment with pincer gap 490. Needle tip 324 is then lowered (not shown), by operation of switch 336, until needle tip distal end 530 touches iris anterior surface 220 (FIG. 22A).

As next depicted in FIG. 22B (with fixation loop 478 held against iris anterior surface 220 by forceps tip 322), needle tip 324 is partially rotated in the clock-wise (CW) direction by operation of switch 338. Such partial rotation of needle tip 324 causes needle tip distal end 530 to penetrate the iris stromal tissue at a narrow entry or engagement line 532. Continued partial CW rotation of needle tip 324 with simultaneous advancement of the needle tip (in the direction of Arrow "H") causes the needle tip to spiral through the engaged iris stromal tissue beneath pincer gap 490 until needle tip distal end 530 subsequently exits the iris tissue at a narrow exit line 534. As described above, in unison with such CW partial rotation of needle tip 324, the needle tip is advanced (by the same operation of switch 338) out of open end 314 of tubular member 308.

In the next operational step illustrated in FIG. 22C with forceps tip 322 still gripping fixation loop 482 and holding the fixation loop against iris anterior surface 220 as described above, and with needle tip 324 still embedded in iris stromal tissue beneath pincer gap 490, the needle tip is lifted (not shown) by operation of switch 336. This lifting of needle tip 324 lifts an iris stromal tissue region 540 into pincer gap 490, thereby lifting and spreading respective ends 486 and 488 of pincer arms 482 and 484 and widening the pincer gap.

Finally, as depicted in FIG. 22D, needle tip 324 is rotated back in the counterclockwise (CCW) direction by operation of switch 338. This operation of switch 338 simultaneously moves (i.e., retracts) needle tip 324 rearwardly (direction of Arrow "H'"), leaving tissue region 540 pinched or trapped in the resulting closing of pincer gap 490 as pincer arms 482 and 464 flex back downwardly toward their original, unflexed position.

At this point, the selected fixation loop 478 has been attached to iris anterior surface 220. Needle tip 324 is then lifted, by operation of switch 336 to clear side 492 of fixation loop 478 and forceps tip upper jaw 346 is opened by operation of switch 334. Instrument 300 may then be repositioned to repeat the above-described attachment procedure on the second fixation loop.

SEPARATION OF OPERATING HEAD PORTION 304—FIGS. 23–25:

The present inventor considers the ability to easily and quickly separate above-described operating head portion 304 (with forceps tip 322 and needle tip 324) from the rest of instrument 300 is desirable (but not essential). Such separation of operating head portion 304 is advantageous for reasons as enabling: (i) the rapid installation of a sterilized operating head portion 304 before each new use of instrument 300, (ii) the efficient sterilization of operating head portion 304, and (iii) the easy replacement of a damaged or worn needle tip 324 and/or forceps tip 322.

Disconnection and reconnection of operating head portion 304 relative to the rest of instrument 300 is provided by detachable connections (described below) between control pins or rods 340, 342 and 344 and their associated connecting pins or rods 341, 343 and 345 and between outer tubular member region 382 and inner housing 436 (FIG. 16).

These detachable connections are identical for each interconnecting pair of control and connecting pins or rods 340 and 341, 342 and 343, and 344 and 345. Consequently, only the detachable connection of a representative pair of control and connecting pins or rods 340 and 341 (for opening and closing forceps tip 322) is depicted in FIGS. 23–26 and described hereinbelow.

Figure 23:
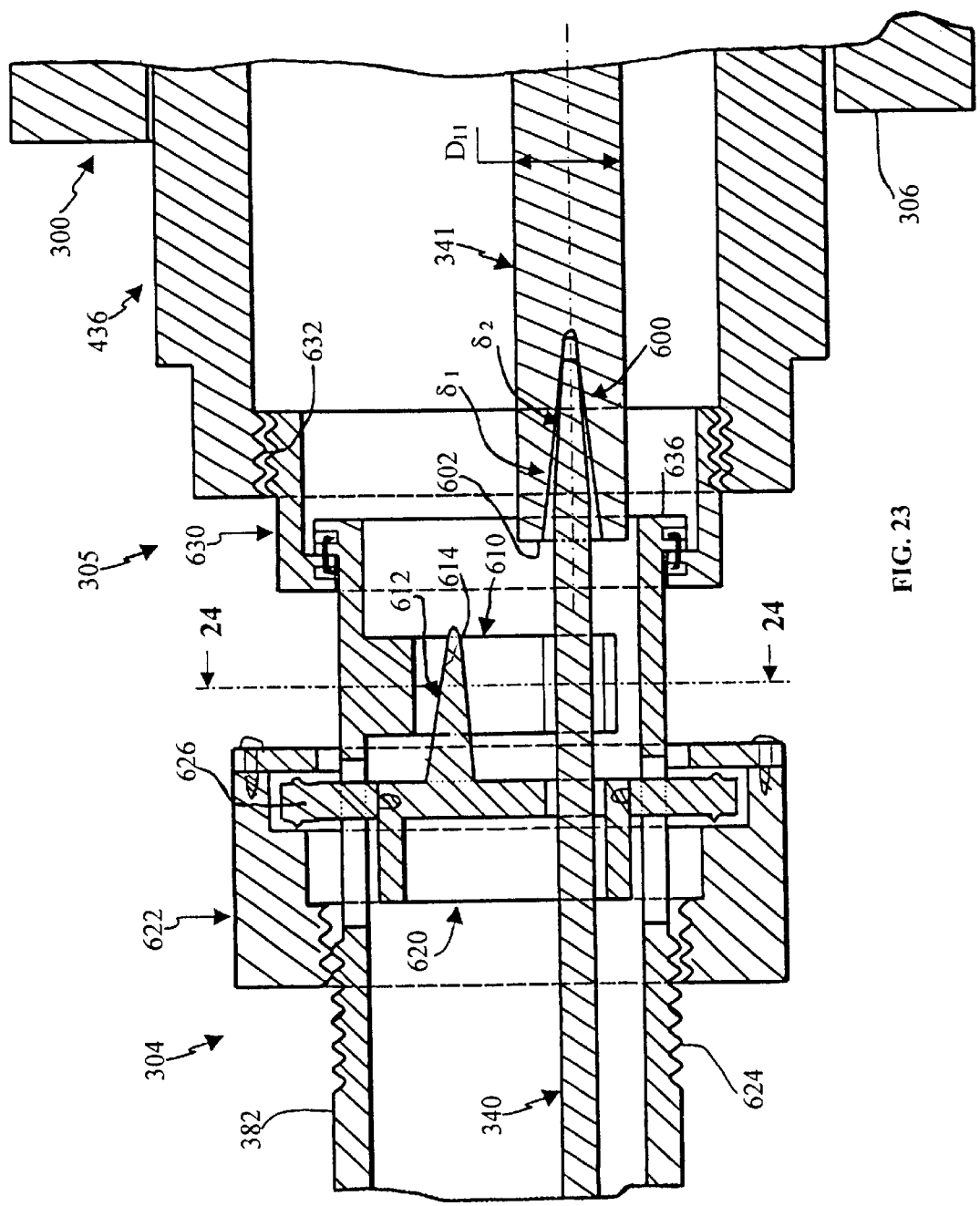
FIG. 23 is a longitudinal cross sectional drawing looking along line 23—23 of FIG. 12 showing internal features of the separation portion of the combination instrument and showing, by way of representative example, the forceps tip control pin frictionally connected to its associated connector pin.

FIG. 23, thus depicts the detachable connection between control pin or rod 340 and associated connecting pin or rod 341, as is required for the controlled opening and closing of forceps tip 322 (not shown) by operation of switch 334 (see FIG. 16). For such detachable connection, a blunt, conical, proximal end 600 of forceps tip control pin or rod 340 is frictionally received or fit into a conically tapered recess or socket 602 formed in a distal end region of connecting pin or rod 341. Preferably, conical proximal end 600 of connecting pin or rod 341 is tapered at tapered at an angle, $\delta_1$, of about 10° and recess 602 is tapered at an angle, $\delta_2$, of about 7°. Connecting pin or rod 341 may have a diameter, $D_{11}$, that is about 2 mm.

With the above-described frictional connection made between control pin or rod 340 and associated connecting pin or rod 341, the control pin or rod can be moved axially by connecting pin or rod 341. However, to permit axial movement of control pin or rod 340, respective first and second jaws 606 and 608 of a spring-loaded control pin clamp 610 (FIG. 24) are held in an open, non-pin gripping position by an axially directed, tapered pin 612 inserted into a mating tapered aperture 614 in the clamp, as shown in both FIGS. 23 and 24.

Tapered pin 612 projects axially rearward from a circular member 620 (as do two hidden, identical tapered pins associated with the two other pairs 342, 343 and 344, 345 of control and connecting pin or rods (also not shown). An internally threaded retaining ring 622 tightened on an externally threaded region 624 of tubular member region 382 maintains (through a circular flange 626 on circular member 620) tapered pin 612 in clamp aperture 614 to hold clamp jaws 606 and 608 open, thereby enabling free axial movement of control pin or rod 340.

An externally threaded ring 630 is threaded into an internally threaded end 632 of internal housing 436. An inwardly-directed flange 634 of ring 630 retains tubular member region 382 in place by bearing against an outwardly-directed flange 636 at the proximal end of member region 382.

Figure 25:
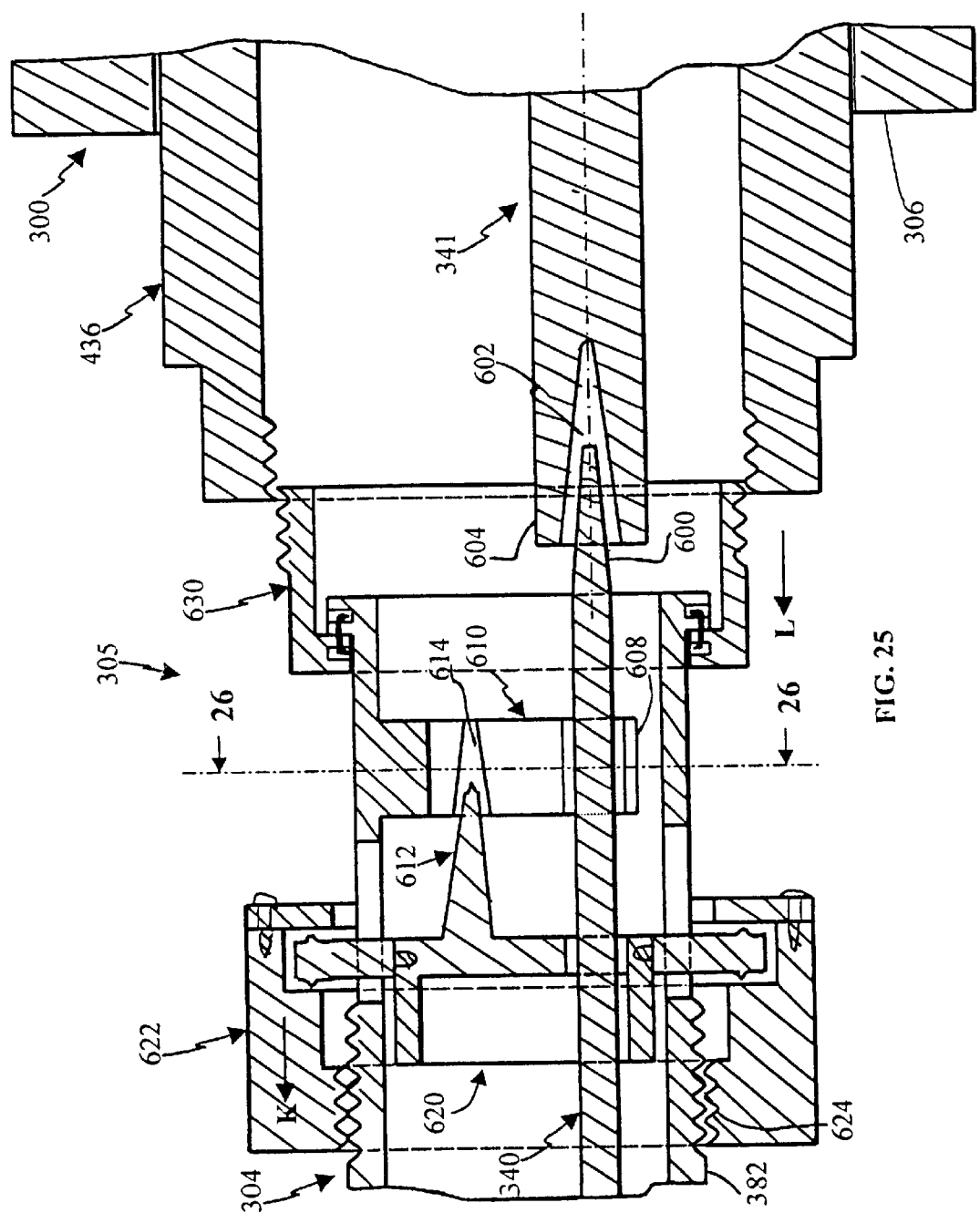
FIG. 25 is a longitudinal cross sectional drawing similar to FIG. 23, but showing the representative control pin clamped by the pin clamping member depicted in FIG. 24 and showing the control pin disconnected from its associated connector pin.

The procedure for detachment of insertion portion 30 304 from internal housing is made obvious from a consideration of FIGS. 25 and 26 and comprises the steps set forth below.

Forceps tip 322 and needle tip 324 are first returned to an initial "zero" or "null" position, by appropriate operation of switches 332, 334, 336 and 338.

Internally threaded ring 622 is then screwed forwardly (direction of Arrow "K") on externally threaded region 624 of tubular member region 382. This forward movement of ring 622 pulls tapered pin 614 (through corresponding forward movement of member 620) out of clamp aperture 614. This permits clamp jaws 606 and 608 to close in a gripping relationship against control rod or pin 340 (FIG. 26). (In the same manner and at the same time, corresponding clamps are clamped against control pins or rods 342 and 344-not shown.)

Externally threaded ring 630 is next unscrewed forwardly (direction of Arrow "L") from internally threaded end 632 of housing 436 to complete the forward separation of insertion portion 304 from housing 436 and thus instrument barrel 306. Note that the clamping by clamp 610 of control pin or rod 340 enables the control pin or rod conical end 600 to be pulled free from connecting pin or rod tapered recess 602 when insertion portion 304 is pulled forwardly from housing 436.

Preferably all above-described parts of insertion portion 304 are constructed of a surgical grade of stainless steel to enable the separated insertion portion to be sterilized by conventional sterilization procedures.

Connection of the same (or another) insertion portion 304 to internal housing 436 is performed by reversing the above-described separation steps.

Although there have been described above an iris fixated IOL and variations thereof, as well as an associated combination enclavation needle and forceps IOL-iris attachment instrument, in accordance with the present invention for purposes of illustrating the manner in which the present invention maybe used to advantage, it is to be understood that the invention is not limited thereto. Consequently, any and all variations and equivalent arrangements which may occur to those skilled in the applicable art are to be considered to be within the scope and spirit of the invention as set forth in the claims which are appended hereto as part of this application.

What is claimed is:

1. A combination forceps and enclavation needle instrument for use in attaching a fixation loop of an anterior chamber intraocular lens (IOL) to an anterior surface of a human ocular iris, said fixation loop having a narrow iris tissue pincer gap defined therein, said instrument comprising:
   a. a handle portion sized for being held in one hand of a user;
   b. a slender ocular insertion portion having an open distal end, said insertion portion being connected to said handle portion;
   c. a forceps tip projecting from said insertion portion open distal end, said forceps tip having first and second IOL gripping jaws connected for gripping said fixation loop;
   d. an enclavation needle tip projecting from said insertion portion open distal end for engaging iris tissue and for lifting said engaged iris tissue into said pincer gap;
   e. operating and control means connected for selectively causing said forceps tip jaws to open and close, for selectively moving said needle tip between a lifted position and a lowered position, and for selectively causing partial rotation of said needle tip in clockwise and counterclockwise directions.

2. The combination forceps and enclavation needle instrument as claimed in claim 1, wherein said operating and control means include moving means for moving said forceps tip and needle tip in unison in a selected axial direction.

3. The combination forceps and enclavation needle instrument as claimed in claim 1, including means for detachably connecting said insertion portion, including said forceps tip and said needle tip, to said handle portion.

4. The combination forceps and enclavation needle instrument as claimed in claim 1, wherein said insertion portion has a major cross sectional dimension of no more than about 2.5 mm.

5. A combination forceps and enclavation needle instrument for use in attaching a fixation loop of an anterior chamber intraocular lens (IOL) to an anterior surface of a human ocular iris, said fixation loop having a narrow iris tissue pincer gap defined therein, said instrument comprising:
   a. a handle portion sized for being held in one hand of a user;
   b. a slender ocular insertion portion having an open distal end, said insertion portion being connected to said handle portion;

c. a forceps tip projecting from said insertion portion open distal end, said forceps tip having first and second IOL gripping jaws connected for gripping said fixation loop;

d. an enclavation needle tip projecting from said insertion portion open distal end for engaging iris tissue and for lifting said engaged iris tissue into said pincer gap, said needle tip having an axial helical shape with a sharp distal end; and e. operating and control means connected for selectively causing said forceps tip jaws to open and close, for selectively moving said needle tip between a lifted position and a lowered position, and for selectively causing partial rotation of said needle tip in clockwise and counterclockwise directions.

6. The combination forceps and enclavation needle instrument as claimed in claimed 5, wherein said operating and control means include means for simultaneously moving said needle tip in an axial direction and for rotating said needle tip.

7. A combination forceps and enclavation needle instrument for use in attaching a fixation loop of an anterior chamber intraocular lens (IOL) to an anterior surface of a human ocular iris, said fixation loop having a narrow iris tissue pincer gap defined therein, said instrument comprising:

a. a handle portion sized for being held in one hand of a user;

b. a slender ocular insertion portion having an open distal end, said insertion portion being connected to said handle portion;

c. a forceps tip projecting from said insertion portion open distal end, said forceps tip having first and second IOL gripping jaws connected for gripping said fixation loop;

d. an enclavation needle tip projecting from said insertion portion open distal end for engaging iris tissue and for lifting said engaged iris tissue into said pincer gap; and e. operating and control means connected for selectively causing said forceps tip jaws to open and close, for selectively moving said needle tip between a lifted position and a lowered position, and for selectively causing partial rotation of said needle tip in clockwise and counterclockwise directions, said operating and control means including an electric power source, a plurality of reversible electric motors and a plurality of electrical switches connected for providing electrical power to said motors from said power source.

8. The combination forceps and enclavation needle instrument as claimed in claim 7, wherein each of said electrical switches comprises a momentary on-off-momentary on switch having a manually operated portion projecting outwardly from said instrument handle portion.

9. The combination forceps and enclavation needle instrument as claimed in claim 8, wherein said manually operated switch portion of each of said plurality of switches project outwardly from said handle portion in locations enabling the operation thereof by one hand of an operator holding said handle portion without the necessity of repositioning said one hand.

10. A combination forceps and enclavation needle instrument for use in attaching a fixation loop of an anterior chamber intraocular lens (IOL) to an anterior surface of a human ocular iris, said fixation loop having a narrow iris tissue pincer gap defined therein, said instrument comprising:

a. a handle portion sized for being held in one hand of a user;

b. a slender ocular insertion portion having an open distal end, said insertion portion being connected to said handle portion;

c. a forceps tip projecting from said insertion portion open distal end, said forceps tip having first and second IOL gripping jaws connected for gripping said fixation loop;

d. an enclavation needle tip projecting from said insertion portion open distal end for engaging iris tissue and for lifting said engaged iris tissue into said pincer gap; and e. operating and control means connected for selectively causing said forceps tip jaws to open and close, for selectively moving said needle tip between a lifted position and a lowered position, and for selectively causing partial rotation of said needle tip in clockwise and counterclockwise directions, said operating and control means including a plurality of manually operated thumb wheels.

11. The combination forceps and enclavation needle instrument as claimed in claim 10, wherein said manually operated thumb wheels extend outwardly from said handle portion in locations enabling the operation thereof by one hand of an operator holding said handle portion without the necessity of repositioning said one hand.

12. A combination forceps and enclavation needle instrument for use in attaching a fixation loop of an anterior chamber intraocular lens (IOL) to an anterior surface of a human ocular iris, said fixation loop having a narrow iris tissue pincer gap defined therein, said instrument comprising:

a. a handle portion sized for being held in one hand of a user;

b. a slender ocular insertion portion having an open distal end, said insertion portion being connected to said handle portion;

c. a forceps tip projecting from said insertion portion open distal end, said forceps tip having first and second IOL gripping jaws connected for gripping said fixation loop;

d. an enclavation needle tip projecting from said insertion portion open distal end for engaging iris tissue and for lifting said engaged iris tissue into said pincer gap; and e. operating and control means connected for selectively causing said forceps tip jaws to open and close, for selectively moving said needle tip between a lifted position and a lowered position, and for selectively causing partial rotation of said needle tip in clockwise and counterclockwise directions, said operating and control means including a first, elongate slender control pin connected to said needle tip and a second, elongate slender control pin pivotally connected to one of said forceps tip jaws.

13. The combination forceps and enclavation needle instrument as claimed in claim 12, wherein said operating and control means include a sleeve slidingly disposed around said first control pin and a third, elongate slender control pin connected to said sleeve, and include means for pivotally connecting said sleeve to a outer tube of said insertion portion, whereby axial movement of said third control pin causes the raising or lowering of said sleeve and said needle tip.

14. A combination forceps and enclavation needle instrument for use in attaching a fixation loop of an anterior chamber intraocular lens (IOL) to an anterior surface of a human ocular iris, said fixation loop having a narrow iris tissue pincer gap defined therein, said instrument comprising:

a. a handle portion sized for being held in one hand of a user;

b. a slender ocular insertion portion having an open distal end and having an outer tubular member, c. a forceps tip projecting from said insertion portion open distal end, said forceps tip having first and second IOL gripping jaws, said first jaw being fixed and said second jaw being connected for movement between an open and a closed position relative to said first jaw;

d. an enclavation needle tip projecting from said insertion portion open distal end;

e. means for detachably connecting said insertion portion, including said needle tip and said forceps tip, to said handle portion;

f. operating and control means connected for selectively causing said second forceps jaw to move between said open and closed positions and for selectively moving said needle tip between a lifted position and a lowered position and for selectively causing partial rotation of said needle tip in clockwise and counterclockwise directions.

15. The combination forceps and enclavation needle instrument as claimed in claim 14, wherein said operating and control means include a first, elongate slender control pin connected to said needle tip and a second, elongate slender control pin pivotally connected to said forceps tip second jaw, said operating and control means further include a sleeve slidingly disposed around said first control pin and a third, elongate slender control pin connected to said sleeve, and means for pivotally connecting said sleeve to said insertion portion outer tubular member, whereby axial movement of said third control pin causes the raising or lowering of said sleeve and said needle tip.

16. The combination forceps and enclavation needle instrument as claimed in claim 14, wherein said operating and control means include a first connecting pin detachably connected to said first control pin, a second connecting pin detachably connected to said second control pin and a third connecting pin detachably connected to said third control pin.

17. The combination forceps and enclavation needle instrument as claimed in claim 16, wherein said operating and control means include respective first, second and third pairs of gears operatively connected to respective ones of said first, second and third connecting pins.

18. The combination forceps and enclavation needle instrument as claimed in claim 17, wherein said operating and control means include respective first, second and third reversible electric motors connected to respective ones of said first, second and third pairs of gears.

19. The combination forceps and enclavation needle instrument as claimed in claim 17, wherein said operating and control means include respective first, second and third thumb wheels connected to said first, second and third pairs of gears.

20. The combination forceps and enclavation needle instrument as claimed in claim 14, wherein said operating and control means include moving means for moving said insertion portion with said forceps tip and needle tip in a selected axial direction.

21. The combination forceps and enclavation needle instrument as claimed in claim 14, wherein said first forceps tip jaw projects further than said forceps tip second jaw from said insertion portion open distal end.

22. The combination forceps and enclavation needle instrument as claimed in claim 14, wherein said insertion portion has an oval cross sectional shape having a major cross sectional dimension of no more than about 2.5 mm.

23. A combination forceps and enclavation needle instrument for use in attaching a fixation loop of an anterior chamber intraocular lens (IOL) to an anterior surface of an ocular iris, said fixation loop being formed having a narrow pincer gap and having thickened end regions, said instrument comprising:

a. a handle portion sized for being held in one hand of a user;

b. a slender ocular insertion portion having an open distal end and having an exterior tubular member and a major cross sectional dimension no greater than about 2.5 mm;

c. forceps tip projecting from said insertion portion open distal end, said forceps tip having first and second IOL gripping jaws said forceps tip jaws being sized for gripping said fixation loop thickened end regions;

d. an enclavation needle tip projecting from said insertion portion open distal end, said needle tip being shaped for engaging iris tissue and for lifting said engaged iris tissue into said fixation loop pincer gap;

e. means for detachably connecting said insertion portion, including said needle tip and said forceps tip, to said handle portion;

f. operating and control means connected for selectively causing said forceps tip jaws to open and close, for selectively moving said needle tip between a lifted position and a lowered position, and for selectively causing partial rotation of said needle tip in clockwise and counterclockwise directions.

24. The combination forceps and enclavation needle instrument as claimed in claim 23, wherein said operating and control means include moving means for moving said forceps tip and needle tip in unison in a selected axial direction.

25. The combination forceps and enclavation needle instrument as claimed in claim 24, wherein said operating and control means include a first, elongate slender control pin connected to said needle tip and a second, elognate slender control pin pivotally connected to said forceps tip second jaw, said operating and control means further include a sleeve disposed around said first control pin and a third, elongate slender control pin connected to said sleeve, and means for pivotally connecting said sleeve to said insertion portion outer tubular member, whereby axial movement of said third control pin causes the raising or lowering of said sleeve and said needle tip.

26. The combination forceps and enclavation needle instrument as claimed in claim 25, wherein said operating and control means include a first connection pin detachably connected to said first control pin, a second connecting pin detachably connected to said second control pin and a third connecting pin detachably connected to said third control pin and further include respective first, second and third pairs of gears operatively connected to said first, second and third connecting pins.

27. The combination forceps and enclavation needle instrument as claimed in claim 23, wherein said needle tip has an axial helical shape with a sharp distal end and wherein said operating and control means include means for simultaneously moving said needle tip in an axial direction and for rotating said needle tip.

28. A hand held instrument for use in attaching a fixation loop of an anterior chamber intraocular lens (IOL) to an anterior surface of a human ocular iris, said fixation loop having a narrow iris tissue pincer gap defined therein, said instrument comprising:

a. a handle portion sized for being held in one hand of a user;

b. a slender ocular insertion portion having an open distal end, said insertion portion being connected to said handle portion;
c. an enclavation needle tip projecting from said insertion portion open distal end, said needle being configured for engaging iris tissue and for lifting said engaged iris tissue into said pincer gap; and
d. operating and control means connected for selectively moving said needle tip between a lifted position and a lowered position, and for selectively causing partial rotation of said needle tip in clockwise and counter-clockwise directions.

29. The hand held instrument as claimed in claim 28, wherein said needle tip has a helical shape in an axial direction with a sharp distal end and wherein said operating and control means include means for simultaneously moving said needle tip in an axial direction and for rotating said needle tip.

30. The hand held instrument as claimed in claim 28, wherein said insertion portion has a major cross sectional dimension of no more than about 2.5 mm.

* * * * *